US008273775B2

(12) United States Patent
Audenaert et al.

(10) Patent No.: US 8,273,775 B2
(45) Date of Patent: Sep. 25, 2012

(54) NON-STEROIDAL BRASSINOSTEROID MIMETIC

(75) Inventors: Dominique Audenaert, Opbrakel (BE); Tom Beeckman, Merelbeke (BE); Bert De Rybel, Nieuwerkerken (BE); Jenny Russinova, Astene (BE); Dirk G. Inze, Moorsel-Aalst (BE)

(73) Assignees: VIB VZW, Ghent (BE); Universiteit Gent, Ghent (BE)

( * ) Notice: Subject to any disclaimer, the term of this patent is extended or adjusted under 35 U.S.C. 154(b) by 468 days.

(21) Appl. No.: 12/311,683

(22) PCT Filed: Oct. 9, 2007

(86) PCT No.: PCT/EP2007/060721
§ 371 (c)(1),
(2), (4) Date: Jan. 15, 2010

(87) PCT Pub. No.: WO2008/049729
PCT Pub. Date: May 2, 2008

(65) Prior Publication Data
US 2010/0152253 A1 Jun. 17, 2010

(30) Foreign Application Priority Data
Oct. 12, 2006 (EP) .................................. 06122151

(51) Int. Cl.
A01N 43/40 (2006.01)
C07D 213/04 (2006.01)
(52) U.S. Cl. ........................................ 514/352; 546/309
(58) Field of Classification Search .................. 514/352; 546/309
See application file for complete search history.

(56) References Cited

U.S. PATENT DOCUMENTS

| 4,117,531 | A | 9/1978 | Ross et al. |
| 6,667,278 | B2 | 12/2003 | Back et al. |
| 7,622,634 | B2 | 11/2009 | Goossens et al. |
| 7,829,758 | B2 | 11/2010 | Cnops et al. |
| 2002/0115570 | A1 | 8/2002 | Back et al. |
| 2006/0029995 | A1 | 2/2006 | Inze et al. |
| 2009/0165167 | A1 | 6/2009 | Goossens et al. |
| 2010/0105561 | A1 | 4/2010 | Audenaert et al. |
| 2010/0170010 | A1 | 7/2010 | Goossens et al. |
| 2011/0078825 | A1 | 3/2011 | Cnops et al. |
| 2011/0307974 | A1 | 12/2011 | Beemster et al. |
| 2011/0314573 | A1 | 12/2011 | de Jaeger et al. |

FOREIGN PATENT DOCUMENTS

| EP | 1 621 629 A | 2/2006 |
| GB | 1 162 727 A | 8/1969 |
| JP | 01075500 | 3/1989 |
| JP | 01 175992 | 7/1989 |
| JP | 06065300 A | 3/1994 |
| JP | 2006 232819 | 9/2006 |
| WO | WO 2008-049729 A1 | 5/2008 |

OTHER PUBLICATIONS

Gortner et al. (CAPLUS Abstract of: Botanical Gazette, (1969), 130(2), 87-97).*
Kato et al., Preparation of glycosyl amino acid derivatives as substrates for sugar transferases, Chemical Abstracts Service. Database accession No. 1994:580239, Columbus, Ohio, US.
Omuaru et al., Reactions of cyclic anhydrides with aromatic primary amines: Part 3, Synthesis of novel 3-(N-arylcarbamoyl)- and 3-(N-naphthylcarbamoyl)carboxylic acids, Chemical Abstracts Service, Database accession No. 1998-775242, Columbus, Ohio, US.
Motoc et al., Sector partition of the molecular Van der Waals space as a measure of steric effects, Chemical Abstracts Service, Database accession No. 1981:14919, Columbus, Ohio, US.
Burduliene et al., Synthesis and antiviral activity of N-aryl-and N-heterylsuccinamino acids and their salts with 2-amino-2-thiazoline, Chemical Abstracts Service, Database accession No. 1997-78364, Columbus, Ohio, US.
Mndzhoyan et al., Derivatives of dibasic carboxylic acids, XVI. 2-Pyridyl- and 4-methyl-2-thiazolylamides of dibasic carboxylic acids, Chemical Abstracts Service, Database accession No. 1957-9323, Columbus, Ohio, US.
Mizufune et al., Method for preparation of unsymmetrical 3-cyano-1, 4-dihydropyridine compounds, Database accession No. 2006:912427, Columbus Ohio, US.
Sivakumar et al., Effect of foliar application of growth regulators on biochemical attributes and grain yield in pearl millet, Biosciences Information Service, Database accession No. PREV200200426298, Philadelphia, PA, US.
PCT International Search Report, PCT/EP2007/060721, dated Jan. 22, 2008.
Co-pending U.S. Appl. No. 10/666,778, filed Sep. 18, 2003, Goossens et al. The use of Genes Encoding Membrane Transporter Pumps to Stimulate the Production of Secondary Metabolites in Biological Cells.
Co-pending U.S. Appl. No. 11/225,709, filed Sep. 12, 2005, Inze et al. A Method for Protein Cleaving Using a Metacaspase Polypeptide.
Co-pending U.S. Appl. No. 11/660,483, filed Apr. 22, 2008, Cnops et al. Modulation of Plant Cell Number.
Co-pending U.S. Appl. No. 11/992,030, filed Mar. 14, 2008, Goossens et al. Means and Methods to Enhance the Production of Vinblastine and Vincristine in Catharanthus Roseus.
Co-pending U.S. Appl. No. 61/190,543, filed Aug. 29, 2008, De Jaeger et al. The AN3 Protein Complex and its use for Plant Growth Promotion.
Co-pending U.S. Appl. No. 61/206,795, filed Feb. 3, 2009, Goossens et al. Genes and Uses Thereof to Modulate Taxane Biosynthesis.

* cited by examiner

Primary Examiner — Robert Havlin
(74) Attorney, Agent, or Firm — TraskBritt

(57) ABSTRACT

The present invention relates to non-steroidal mimetics of brassinosteroids. More specifically, it relates to non-steroidal monocyclic compounds, capable of rescuing the brassinosteroid receptor null mutation bri1-116. Preferably, said compounds are low molecular weight, monocyclic halogenated compound.

3 Claims, 17 Drawing Sheets

Figure 1
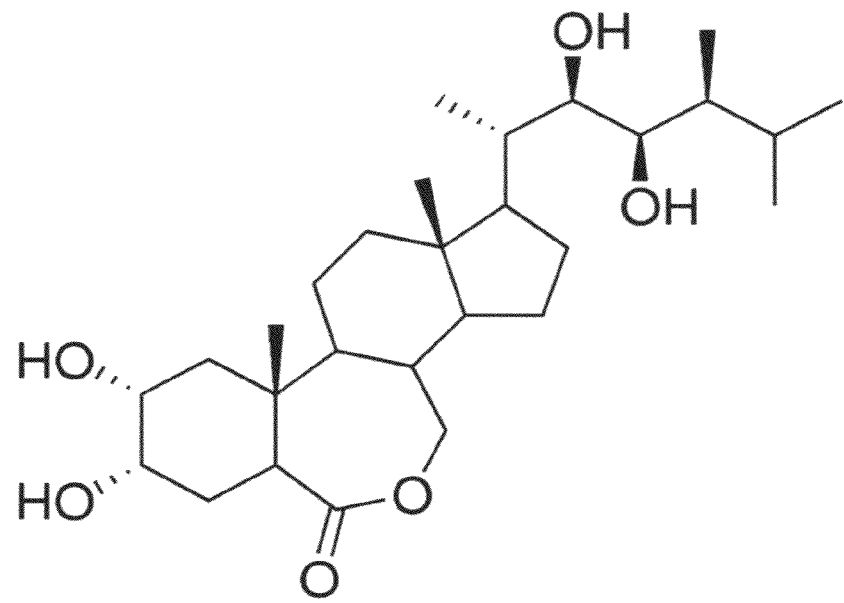
Figure 2 (according to Wang, X. & Chory, J. *Science* 313, 1118-1122 (2006))
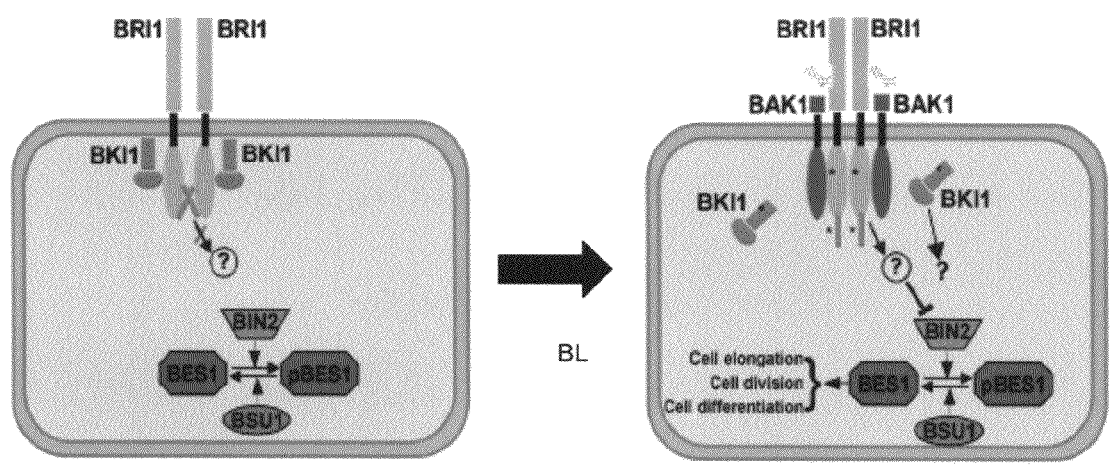

Figure 3
A
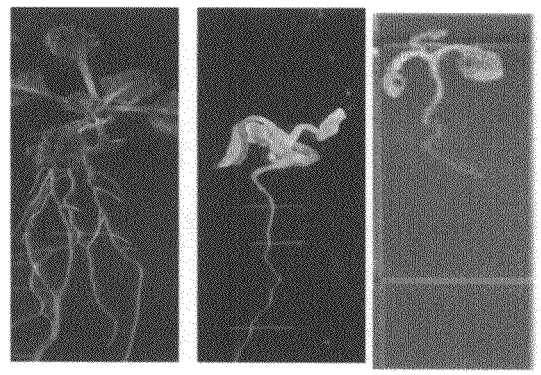
B
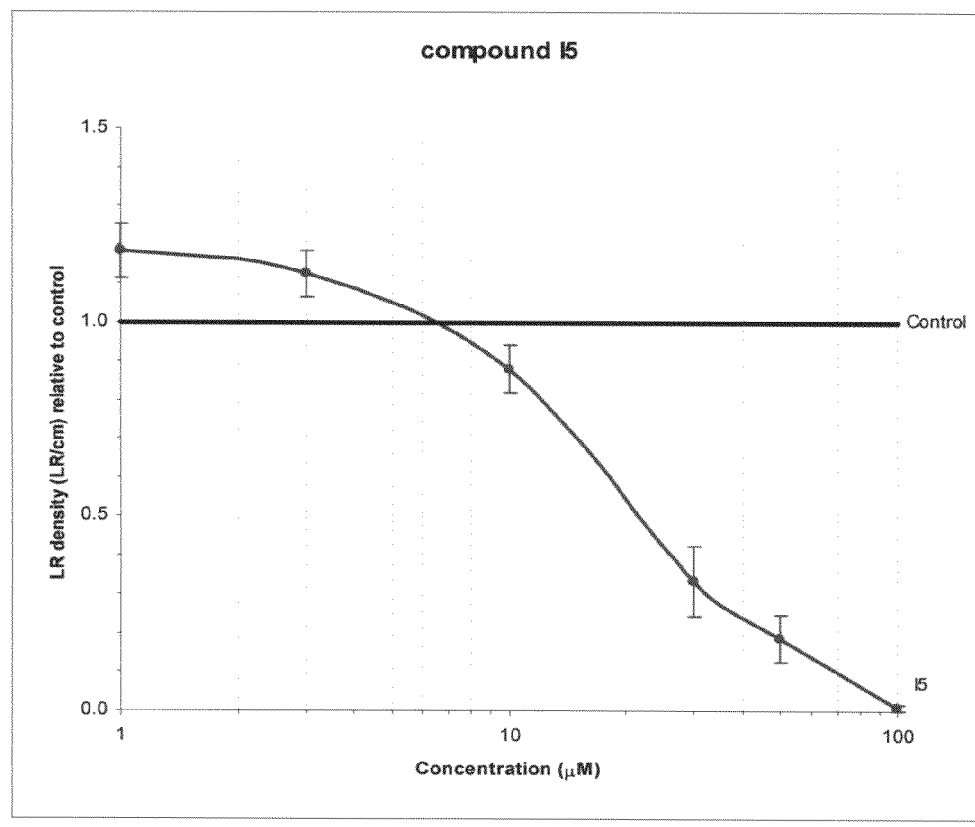

Figure 9
I05 VAR1
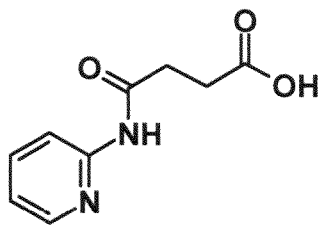
I05 VAR5
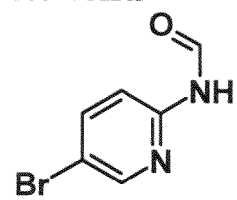
I05 VAR2
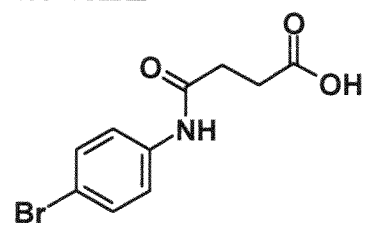
I05 VAR6
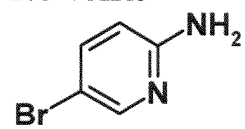
I05 VAR3
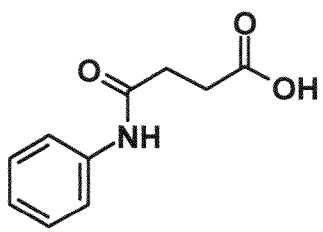
I05 VAR7
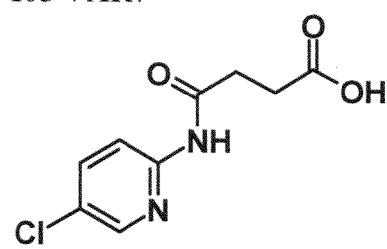
I05 VAR4
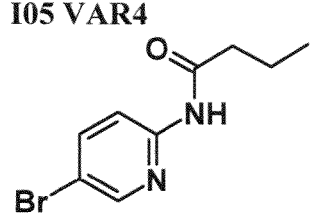
I05 VAR8
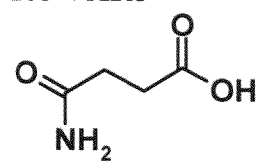

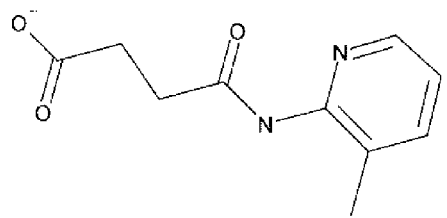
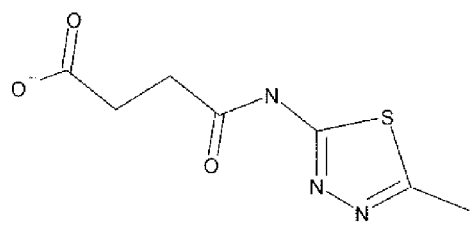
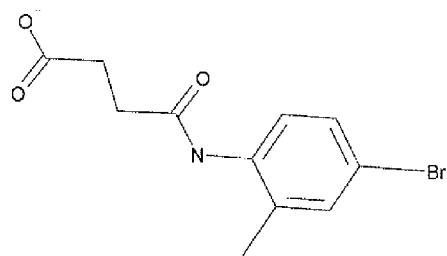
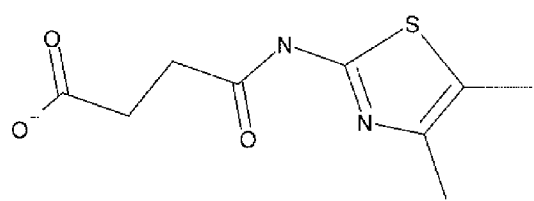
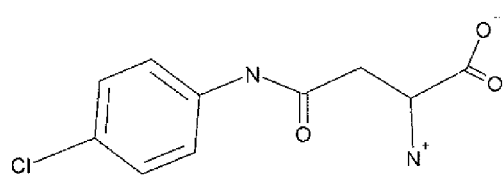
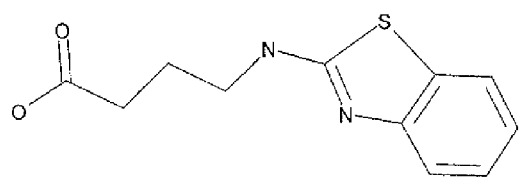
FIG. 11

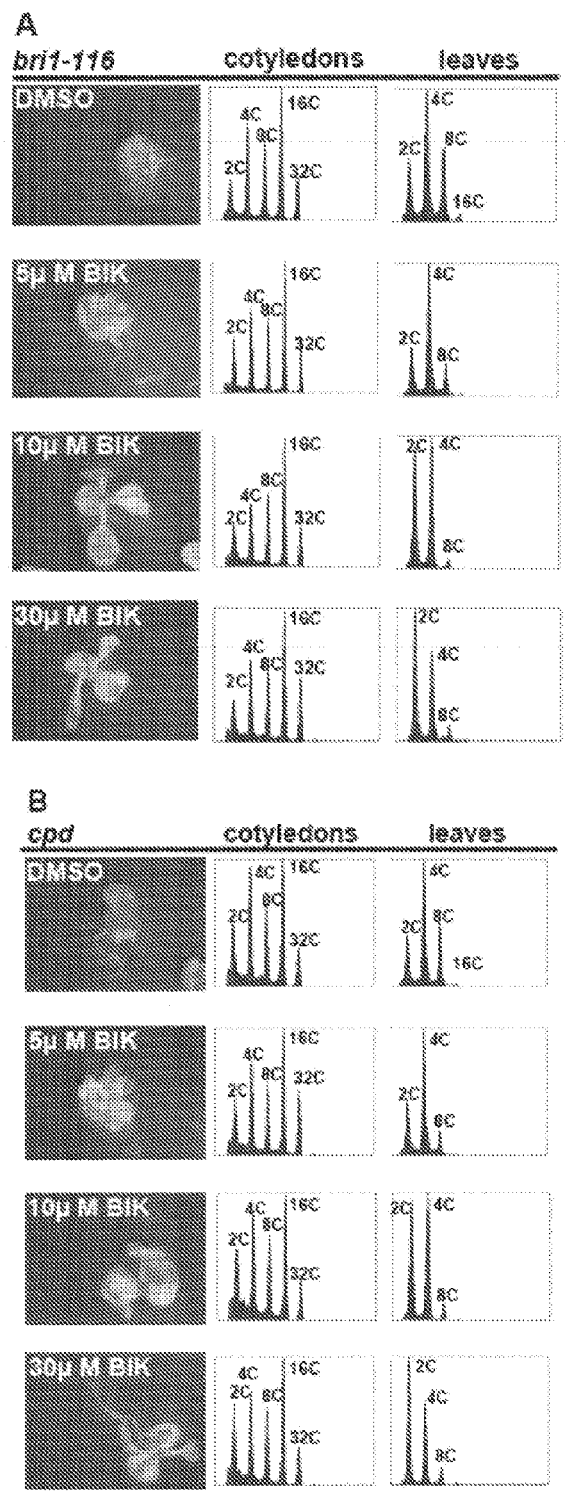
FIG. 16 (page 1 of 2)

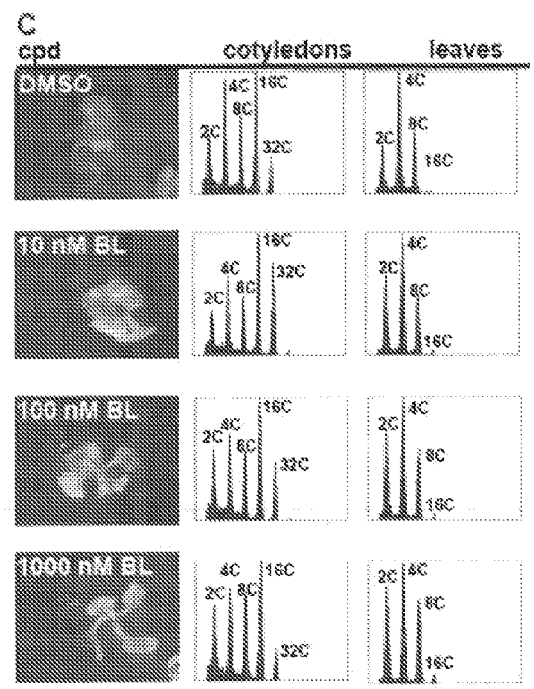
FIG. 16 (page 2 of 2)

Figure 17
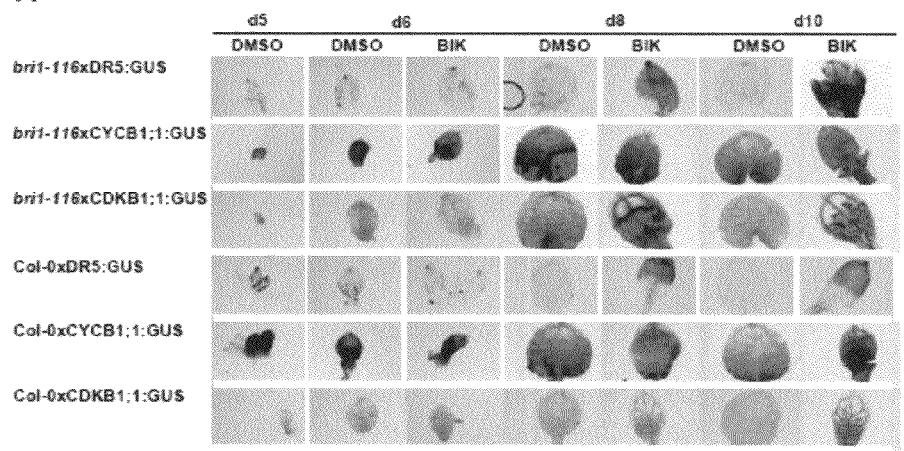
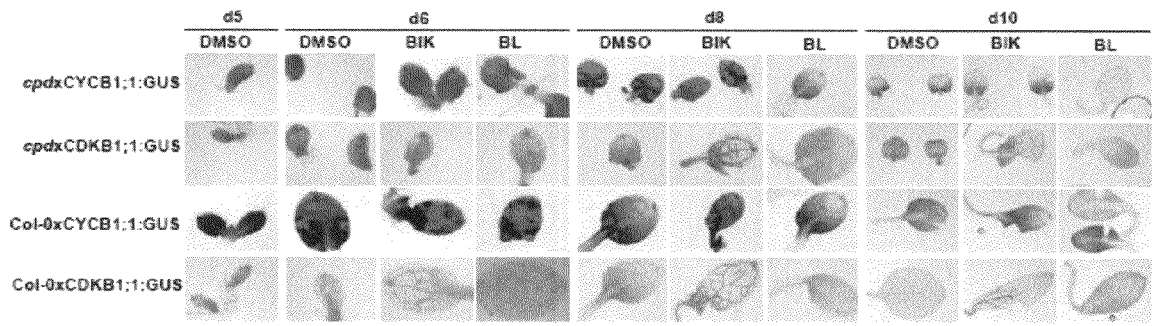

SEQUENCE LISTING

```
<160> NUMBER OF SEQ ID NOS: 31

<210> SEQ ID NO 1
<211> LENGTH: 20
<212> TYPE: DNA
<213> ORGANISM: Artificial
<220> FEATURE:
<223> OTHER INFORMATION: BAS1 primer

<400> SEQUENCE: 1
ttggcttcat accgtttggc                                                 20

<210> SEQ ID NO 2
<211> LENGTH: 22
<212> TYPE: DNA
<213> ORGANISM: Artificial
<220> FEATURE:
<223> OTHER INFORMATION: BAS1 primer

<400> SEQUENCE: 2
ttacagcgag tgtcaatttg gc                                              22
```

```
<210> SEQ ID NO 3
<211> LENGTH: 18
<212> TYPE: DNA
<213> ORGANISM: Artificial
<220> FEATURE:
<223> OTHER INFORMATION: BR6Ox1 primer

<400> SEQUENCE: 3
tggccaatct ttggcgaa                                                 18

<210> SEQ ID NO 4
<211> LENGTH: 21
<212> TYPE: DNA
<213> ORGANISM: Artificial
<220> FEATURE:
<223> OTHER INFORMATION: BR6Ox1 primer

<400> SEQUENCE: 4
tcccgtatcg gagtctttgg t                                             21

<210> SEQ ID NO 5
<211> LENGTH: 24
<212> TYPE: DNA
<213> ORGANISM: Artificial
<220> FEATURE:
<223> OTHER INFORMATION: BR6Ox2 primer

<400> SEQUENCE: 5
caatagtctc aatggacgca gagt                                          24

<210> SEQ ID NO 6
<211> LENGTH: 20
<212> TYPE: DNA
<213> ORGANISM: Artificial
<220> FEATURE:
<223> OTHER INFORMATION: BR6Ox2 primer

<400> SEQUENCE: 6
aaccgcagct atgttgcatg                                               20

<210> SEQ ID NO 7
<211> LENGTH: 21
<212> TYPE: DNA
<213> ORGANISM: Artificial
<220> FEATURE:
<223> OTHER INFORMATION: BRI1 primer

<400> SEQUENCE: 7
ggtgaaacag cacgcaaaac t                                             21

<210> SEQ ID NO 8
<211> LENGTH: 20
<212> TYPE: DNA
<213> ORGANISM: Artificial
<220> FEATURE:
<223> OTHER INFORMATION: BRI1 primer

<400> SEQUENCE: 8
cacgcaaccg caactttaa                                                20

<210> SEQ ID NO 9
<211> LENGTH: 22
<212> TYPE: DNA
<213> ORGANISM: Artificial
<220> FEATURE:
<223> OTHER INFORMATION: CPD

<400> SEQUENCE: 9
```

```
cccaaaccac ttcaaagatg ct                                            22

<210> SEQ ID NO 10
<211> LENGTH: 20
<212> TYPE: DNA
<213> ORGANISM: Artificial
<220> FEATURE:
<223> OTHER INFORMATION: CPD primer

<400> SEQUENCE: 10
gggcctgtcg ttaccgagtt                                               20

<210> SEQ ID NO 11
<211> LENGTH: 23
<212> TYPE: DNA
<213> ORGANISM: Artificial
<220> FEATURE:
<223> OTHER INFORMATION: DWF4 primer

<400> SEQUENCE: 11
gtgatctcag ccgtacattt gga                                           23

<210> SEQ ID NO 12
<211> LENGTH: 24
<212> TYPE: DNA
<213> ORGANISM: Artificial
<220> FEATURE:
<223> OTHER INFORMATION: DWF4 primer

<400> SEQUENCE: 12
cacgtcgaaa aactaccact tcct                                          24

<210> SEQ ID NO 13
<211> LENGTH: 19
<212> TYPE: DNA
<213> ORGANISM: Artificial
<220> FEATURE:
<223> OTHER INFORMATION: ROT3 primer

<400> SEQUENCE: 13
attggcgcgt tcctcagat                                                19

<210> SEQ ID NO 14
<211> LENGTH: 22
<212> TYPE: DNA
<213> ORGANISM: Artificial
<220> FEATURE:
<223> OTHER INFORMATION: ROT3 primer

<400> SEQUENCE: 14
caagacgcca aagtgagaac aa                                            22

<210> SEQ ID NO 15
<211> LENGTH: 23
<212> TYPE: DNA
<213> ORGANISM: Artificial
<220> FEATURE:
<223> OTHER INFORMATION: BES1 primer

<400> SEQUENCE: 15
caacctcgcc taccttcaat ctc                                           23

<210> SEQ ID NO 16
<211> LENGTH: 25
<212> TYPE: DNA
<213> ORGANISM: Artificial
```

```
<220> FEATURE:
<223> OTHER INFORMATION: BES1 primer

<400> SEQUENCE: 16
ttggctgttc tcaaacttaa actcg                                         25

<210> SEQ ID NO 17
<211> LENGTH: 21
<212> TYPE: DNA
<213> ORGANISM: Artificial
<220> FEATURE:
<223> OTHER INFORMATION: BIN2 primer

<400> SEQUENCE: 17
gtgactttgg cagtgcgaaa c                                             21

<210> SEQ ID NO 18
<211> LENGTH: 25
<212> TYPE: DNA
<213> ORGANISM: Artificial
<220> FEATURE:
<223> OTHER INFORMATION: BIN2 primer

<400> SEQUENCE: 18
cagcattttc tccgggaaat aatgg                                         25

<210> SEQ ID NO 19
<211> LENGTH: 22
<212> TYPE: DNA
<213> ORGANISM: Artificial
<220> FEATURE:
<223> OTHER INFORMATION: BSU1 primer

<400> SEQUENCE: 19
ggcggttttc gtcaacaatt cc                                            22

<210> SEQ ID NO 20
<211> LENGTH: 25
<212> TYPE: DNA
<213> ORGANISM: Artificial
<220> FEATURE:
<223> OTHER INFORMATION: BSU1 primer

<400> SEQUENCE: 20
ccatctaaac tgatctcggg taagg                                         25

<210> SEQ ID NO 21
<211> LENGTH: 25
<212> TYPE: DNA
<213> ORGANISM: Artificial
<220> FEATURE:
<223> OTHER INFORMATION: BZR1 primer

<400> SEQUENCE: 21
cctctacatt cttcccttte ctcag                                         25

<210> SEQ ID NO 22
<211> LENGTH: 25
<212> TYPE: DNA
<213> ORGANISM: Artificial
<220> FEATURE:
<223> OTHER INFORMATION: BZR1 primer

<400> SEQUENCE: 22
gcttagcgat agattcccag ttagg                                         25
```

```
<210> SEQ ID NO 23
<211> LENGTH: 24
<212> TYPE: DNA
<213> ORGANISM: Artificial
<220> FEATURE:
<223> OTHER INFORMATION: CDKA1;1 primer

<400> SEQUENCE: 23
attgcgtatt gccactctca tagg                                          24

<210> SEQ ID NO 24
<211> LENGTH: 22
<212> TYPE: DNA
<213> ORGANISM: Artificial
<220> FEATURE:
<223> OTHER INFORMATION: CDKA1;1 primer

<400> SEQUENCE: 24
tcctgacagg gataccgaat gc                                            22

<210> SEQ ID NO 25
<211> LENGTH: 22
<212> TYPE: DNA
<213> ORGANISM: Artificial
<220> FEATURE:
<223> OTHER INFORMATION: EEF1 primer

<400> SEQUENCE: 25
ctggaggttt tgaggctggt at                                            22

<210> SEQ ID NO 26
<211> LENGTH: 21
<212> TYPE: DNA
<213> ORGANISM: Artificial
<220> FEATURE:
<223> OTHER INFORMATION: EEF1 primer

<400> SEQUENCE: 26
ccaagggtga aagcaagaag a                                             21

<210> SEQ ID NO 27
<211> LENGTH: 16
<212> TYPE: DNA
<213> ORGANISM: Artificial
<220> FEATURE:
<223> OTHER INFORMATION: BKI1 primer

<400> SEQUENCE: 27
gctccggcgt cgatga                                                   16

<210> SEQ ID NO 28
<211> LENGTH: 20
<212> TYPE: DNA
<213> ORGANISM: Artificial
<220> FEATURE:
<223> OTHER INFORMATION: BKI1 primer

<400> SEQUENCE: 28
gacgatagtc cggccgtaga                                               20

<210> SEQ ID NO 29
<211> LENGTH: 27
<212> TYPE: DNA
<213> ORGANISM: Artificial
<220> FEATURE:
<223> OTHER INFORMATION: Full length BSU1 primer

<400> SEQUENCE: 29
```

```
gtgaattcgc tcctgatcaa tcttatc                                    27

<210> SEQ ID NO 30
<211> LENGTH: 27
<212> TYPE: DNA
<213> ORGANISM: Artificial
<220> FEATURE:
<223> OTHER INFORMATION: Full length BSU1 primer

<400> SEQUENCE: 30
gagaattcca taagaaggtc atttcga                                    27

<210> SEQ ID NO 31
<211> LENGTH: 27
<212> TYPE: DNA
<213> ORGANISM: Artificial
<220> FEATURE:
<223> OTHER INFORMATION: Full length BSU1 primer

<400> SEQUENCE: 31
cgagtcgacc ctttattcac ttgactc                                    27
```

NON-STEROIDAL BRASSINOSTEROID MIMETIC

The present invention relates to non-steroidal mimetics of brassinosteroids. More specifically, it relates to non-steroidal monocyclic compounds, capable of rescuing the brassinosteroid receptor null mutation bri1-116. Preferably, said compounds are low molecular weight, monocyclic halogenated compounds.

Brassinosteroids (BRs), such as Brassinolide, 24-Epi-brassinolide, 28-Homobrassinolide and Castasterone, are plant hormones involved in multiple developmental processes. Brassinosteroids are, amongst others, involved in plant growth promotion, increase in the success of fertilization, shortening the period of vegetative growth, improvement of fruit quality, increase of stress resistance and crop yield increase (Khripach et al., 2000).

BRs are a group of naturally occurring polyhydroxy steroids. Natural BRs have essentially a common 5-alpha cholestan skeleton (FIG. 1) and their structural variations come from the kind and orientation of functionalities on the skeleton, and from variations in the B ring. BRs exert their activity by binding to the plasma membrane receptor kinase BRI1, resulting in the activation of a signalling pathway that involves a glycogen synthase kinase-3-like kinase (BIN2) and a serine/threonine phosphatase BSU1. BIN2 negatively regulates BR signalling by phosphorylation of the transcription factors BES1 (and probably the closely related BZR1), while dephosphorylation of BES1 by BSU1 activates the transcription of BR induced genes (Clouse, 2002; Vert and Chory, 2006; FIG. 2)

Due to their importance as plant growth promoting compounds, several companies developed production methods for BRs and BR analogues. Such methods have been disclosed, amongst others, in JP01075500, JP01175992 and U.S. Pat. No. 6,667,278. However, those synthetic BRs and BR analogues are generally too expensive for large scale commercial applications. Therefore, there is a clear interest in low molecular weight, non-steroidal compounds with BR activity. Non steroidal mimetics of brassinolide have been disclosed in U.S. Pat. No. 6,667,278. However, although those structures do not longer have the canonical 5-alpha cholestan skeleton, the molecules are rather complex and include two bicyclic subunits, each having a vicinal diol group and a polar unit. Said compounds are supposed to bind and act on the BR receptor, as is stated that the vicinal diol group and the polar group should be linked by a linking moiety such that the vicinal diol groups and polar unit are closely superimposable on corresponding functional groups in the brassinosteroid.

Using a chemical genetics approach, surprisingly we found non-steroidal, monocyclic low molecular weight compounds, having BR activity. Even more surprisingly, those compounds do not exert their activity by the BR receptor, as they can rescue the bri1 mutation.

A first aspect of the invention is a non-steroidal, monocyclic brassinosteroid mimetic, having the formula

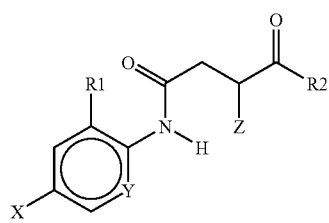

whereby (a) X represents hydrogen or a halogen (b) Y represent carbon or nitrogen (c) Z represents hydrogen or a positively charged nitrogen (d) $R_1$ represents hydrogen or a methyl group and (e) $R_2$ represents hydrogen, a hydroxyl, methyl or carboxy group. Preferably, said non-steroidal monocyclic brassinosteroid mimetic is 4-[(5-fluoro-2-pyridinyl)amino]-4-oxobutanoic acid. A brassinosteroid mimetic, as used here, means that the compound can be used to replace brassinosteroids such as, but not limited to brassinolide, to treat plants, in order to obtain the phenotypical effects of BR treatment. These phenotypical effects are known to the person skilled in the art, and include, but not limited to plant growth promotion, increase of yield of grain and fruit crops and induction of drought and freeze resistance.

Another aspect of the invention is the use of a non-steroidal, monocyclic compound to induce brassinosteroid depending gene expression. Brassinosteroid depending gene expression as used here means both brassinosteroid depending gene induction as well as brassinosteroid depending gene repression. Brassinosteroid depending genes are under control of the BES1 and/or BZR1 transcription factors. Preferably, said genes comprise a BR response element GGTG(T/C)G (He et al., 2005; Wang et al., 2006). Preferably, said non-steroidal, monocyclic compound is inducing BES1 dephosphorylation. Even more preferably, said induction of brassinosteroid depending gene expression and/or said BES1 dephosphorylation is independent from the brassinosteroid receptor BRI1. A preferred embodiment is the use of a non-steroidal, monocyclic compound according to the invention, whereby said compound has the formula

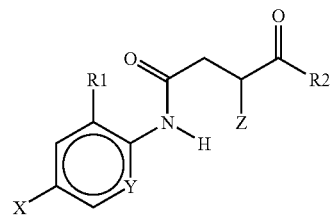

whereby (a) X represents hydrogen or a halogen (b) Y represent carbon or nitrogen (c) Z represents hydrogen or a positively charged nitrogen (d) $R_1$ represents hydrogen or a methyl group and (e) $R_2$ represents hydrogen, a hydroxyl, methyl or carboxy group. Preferably, said compound is selected from the group consisting of 4-[(5-fluoro-2-pyridinyl)amino]-4-oxobutanoic acid, 4-[(5-chloro-2-pyridinyl)amino]-4-oxobutanoic acid, 4-[(5-bromo-2-pyridinyl)amino]-4-oxobutanoic acid and 4-[(5-iodo-2-pyridinyl)amino]-4-oxobutanoic acid.

Still another aspect of the invention is the use of a non-steroidal, monocyclic brassinosteroid mimetic according to the invention to derive in silico compounds with a brassinosteroid mimetic activity. Indeed, by using the program ROCS (Open Eye Scientific Software, USA), as a non-limiting example, to perform a shape-based virtual screening novel compounds that have a similar functionality can be identified. All compounds with a shape-based Tanimoto similarity higher than 0.8 can be selected. Examples of such compounds are given in the application. Another aspect of the invention is a composition for promoting plant growth, comprising a non-steroidal, monocyclic brassinosteroid mimetic according to the invention. Said composition might be an aqueous solution comprising said brassinosteroid mimetic, or a composition comprising any other suitable vector. The composition may further comprise other plant growth regulators such as auxins, cytokinins or gibberellins. Preferably said composition is comprising a non-steroidal, monocyclic compound selected from a group consisting of 4-[(5-fluoro-2-pyridinyl)amino]-4-oxobutanoic acid, 4-[(5-chloro-2-pyridinyl)amino]-4-oxobutanoic acid, 4-[(5-bromo-2-pyridinyl)amino]-4-oxobutanoic acid and 4-[(5-iodo-2-pyridinyl)amino]-4-oxobutanoic acid.

Still another aspect of the invention is a method for promoting plant growth and/or increasing crop yield by applying to the plant an effective amount of the non-steroidal, monocyclic brassinosteroid mimetic according to the invention. The promotion of the plant growth can be direct, by stimulation of the cell division, or indirect, such as by increasing abiotic stress resistance. Increase of yield can be increase of plant biomass, or increase of grain or fruit yield. Preferably, said non-steroidal, monocyclic brassinosteroid mimetic is selected from a group consisting of 4-[(5-fluoro-2-pyridinyl)amino]-4-oxobutanoic acid, 4-[(5-chloro-2-pyridinyl)amino]-4-oxobutanoic acid, 4-[(5-bromo-2-pyridinyl)amino]-4-oxobutanoic acid and 4-[(5-iodo-2-pyridinyl)amino]-4-oxobutanoic acid.

BRIEF DESCRIPTION OF THE FIGURES

FIG. 1: Chemical structure of brassinolide (BL).

FIG. 2: Diagram of the brassinosteroid signal transduction pathway (according to X. Wang and J. Chory, 2006).

FIG. 3: (A) Phenotypic characterization. WT plants were grown under standard conditions on agar plates. After 3 days of germination, plants were transferred to agar plates containing abrasin (I5) at a concentration of 50 µM or brassinolide (BL) at a concentration of 1 µM. Left panel: control plant. Middle panel: abrasin treated plant. Right panel: BL treated plant. (B) Dose response measurements of abrasin using lateral root formation as an indicator of brassinosteroid like activity. Error bars represent standard error of the mean.

FIG. 9: Abrasin derivatives.

FIG. 11: In silico derived compounds with potential brassinosteroid mimetic activity.

FIG. 16: Rescue of bri1-116 and cpd mutants grown on different concentrations of ABRASIN and BL. The plants were germinated on MS+DMSO medium till day 5 and afterwards transferred on MS supplemented with the respective concentration of ABRASIN and BL for 6 more days. Flowcytometric analysis of cotyledons and leaves was performed at the last day of treatments. (A.) Rescue of bri1-116 mutants by ABRASIN. Increasing the ABRASIN concentration promotes cell division activation. (B.) Rescue of cpd mutants by ABRASIN. Increasing the ABRASIN concentration promotes cell division activation. (C.) Rescue of cpd mutants by BL. Both cell division and endoreduplication take place in the BL rescue strategy. BL: brassinolide; BIK: abrasin.

FIG. 17: Investigation of differences in the rescue strategy of bri1-116 and cpd mutants treated with ABRASIN (30 µM) or BL (1 µM). The activation of markers for auxin response (DR5) and cell division (CYCB1; 1 and CDKB1; 1) was followed by localization of their promoters fused to β-glucuronidase (GUS) reporter gene. The first leaf was observed for comparison between all the treatments. Samples for GUS assay were taken on day 6th (i.e. 1 day treatment), 8th (i.e. 3 days treatment), 10th (i.e. 5 days treatment). (A.) The effect of ABRASIN on the first leaf of bri1-116 and Col-0 plants—activity localization of DR5, CYCB1; 1 and CDKB1; 1 promoters fused to GUS reporter gene (B.) The effect of ABRASIN on the first leaf of cpd and Col-0 plants—activity localization of CYCB1; 1 and CDKB1; 1 promoters fused to GUS reporter gene. BL: brassinolide; BIK: abrasin.

EXAMPLES

Materials and Methods to the Examples

Chemical Genetics Screening and Growth Conditions

Figure 4:
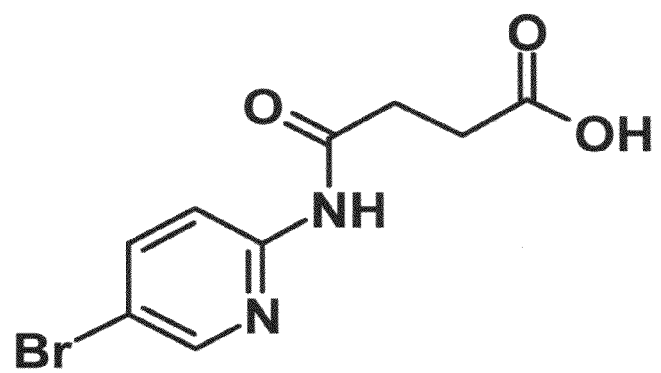
FIG. 4: Chemical structure of abrasin (4-[(5-bromo-2-pyridinyl)amino]-4-oxobutanoic acid).

A commercial 10.000 compound library (DiverSet, ChemBridge, USA) was screened for brassinosteroid related phenotypes. Three to four *Arabidopsis thaliana* (L.) Heynh. seeds were sown in 96-well filterplates (Multiscreen HTS MSBVS1210, Millipore, USA) in liquid medium derived from standard Murashige and Skoog (MS) medium in a growth chamber under continuous light (110 $\mu$E.m$^2$. s$^1$ photosynthetically active radiation, supplied by cool-white fluorescent tungsten tubes; Osram) at 22° C. Three days after germination compounds were added to the 96-well plates at a final concentration of 50 $\mu$M. Plants were screened six days after germination for brassinosteroid-related phenotypes.

For further phenotypical analysis, all plants were grown on vertically oriented square plates (Greiner Labortechnik, Austria) with solid medium derived from standard Murashige and Skoog medium under the same conditions. For the hypocotyl-elongation assay, plants were grown in the dark at 22° C. under the same conditions.

Abrasin, Derivatives and Other Compounds

Abrasin and all derivative molecules were purchased from ChemBridge, USA (ChemBridge ID Abrasin: 5122035, Var2: 5122029, Var3: 5133967, Var4: 5843203, Var6: 5121777 and Var7: 5310341). Epibrassinolide (BL) and cycloheximide (CHX) were purchased from Sigma, USA. The proteasome inhibitor MG132 (Z-Leu-Leu-Leu-CHO) was purchased from BostonBiochem, USA.

Western Blotting

For protein extraction, six-day-old seedlings were grown under standard conditions as described earlier on solid medium. Plants were next soaked in liquid MS-medium supplemented with the indicated compounds (concentrations and time periods as indicated in figures). Subsequently, plants were frozen in liquid nitrogen, ground and homogenized in ice-cold homogenization buffer (25 mM Tris-HCl (pH 8), 5 mM EDTA, 1 mM $\beta$-Mercapto-ethanol, 15 mM MgCl$_2$, 85 mM NaCl, 0.1% Tween 20, 1 protease inhibitor tablet/50 ml, Complete (Roche diagnostics, Belgium)). The homogenate was centrifuged twice (5 min, 14.000 rpm, 4° C.) in an Eppendorf Centrifuge 5417. Loading buffer was added, the samples were heated for 10 min at 95° C. and centrifuged. The samples were separated on a 12% acrylamide gel or a 4-20% gradient pre-cast gel (Bio-Rad) and blotted on nitrocellulose membranes (Hybond-C super, GE-Biosciences, UK) in 190 mM glycine and 25 mM Tris-Hcl using a mini-blotting system (Bio-Rad, USA) for 1 h. Membranes were blocked overnight at 4° C. in phosphate buffer with 0.1% Tween 20 and 5% skim milk (BD Difco, USA). For immunodetection, anti-BES1 antibodies at 1:2000 dilution and anti-GFP antibodies at 1:1000 dilution were used as primary antibody. As secondary antibody, anti-rat and anti-rabbit were used at 1:10.000 dilution. The proteins were detected by chemiluminescence (Perkin-Elmer, USA).

Real Time PCR

RNA was extracted with the RNeasy kit. Poly(dT) cDNA was prepared from 1 mg of total RNA with Superscript III reverse transcriptase (Invitrogen) and quantified on an LightCycler 480 apparatus (Roche) with the SYBR Green I Master kit (Roche) according to the manufacturer's instructions. Target quantifications were performed with specific primer pairs designed with the Beacon Designer 4.0 (Premier Biosoft International). All PCRs were performed in triplicate. Expression levels were normalized to EEF1$\alpha$ and CDKA1; 1 expression levels that did not show clear systematic changes in Ct value.

The primers used to quantify gene expression levels were for BAS 1: 5'-TTGGCTTCATACCGTTTGGC-3' and 5'-TTACAGCGAGTGTCAATTTGGC-3'; BR6Ox1: 5'-TGCCAATCTTTGGCGAA-3' and 5'-TCCCGTATCGGAGTCTTTGGT-3'; BR6Ox2: 5'-CAATAGTCTCAATGGACGCAGAGT-3' and 5'-AACCGCAGCTATGTTGCATG-3'; BRI1: 5'-GGTGAAACAGCACGCAAAACT-3' and 5'-CACGCAACCGCAACTTTTAA-3'; CPD: 5'-CCCAAACCACTTCAAAGATGCT-3' and 5'-GGGCCTGTCGTTACCGAGTT-3'; DWF4: 5'-GTGATCTCAGCCGTACATTTGGA-3' and 5'-CACGTCGAAAAACTACCACTTCCT-3' ROT3: 5'-ATTGGCGCGTTCCTCAGAT-3' and 5'-CAAGACGCCAAAGTGAGAACAA-3'; BES1: 5'-CAACCTCGCCTACCTTCAATCTC-3' and 5'-TTGGCTGTTCTCAAACTTAAACTCG-3'; BIN2: 5'-GTGACTTTGGCAGTGCGAAAC-3' and 5'-CAGCATTTTCTCCGGGAAATAATGG-3'; BSU 1: 5'-GGCGGTTTTCGTCAACAATTCC-3' and 5'-CCATCTAAACTGATCTCGGGTAAGG-3'; BZR1: 5'-CCTCTACATTCTTCCCTTTCCTCAG-3' and 5'-GCTTAGCGATAGATTCCCAGTTAGG-3'; CDKA1; 1: 5'-ATTGCGTATTGCCACTCTCATAGG-3' and 5'-TCCTGACAGGGATACCGAATGC-3'; EEF1$\alpha$: 5'-CTGGAGGTTTTGAGGCTGGTAT-3' and 5'-CCAAGGGTGAAAGCAAGAAGA-3'; BKI1: 5'-GCTCCGGCGTCGATGA-3' and 5'-GACGATAGTCCGGCCGTAGA-3'.

Kinase Assay

For in vitro kinase assays, MBP, MBP-BES1, and MBP-bes1 (20 ng each) were incubated with GST-BIN2 or GST-BRI1 kinase (200 ng each) in 20 $\mu$l of kinase buffer (20 mM Tris [pH 7.5], 100 mM NaCl, and 12 mM MgCl2) and 10 $\mu$Ci $^{32}$P-$\gamma$ATP. After incubation at 37° C. for 40 min, the reactions were stopped by adding 20 $\mu$l of 2×SDS buffer and boiling at 94° C. for 5 min. Proteins were resolved by a PAGE gel and phosphorylation was detected by exposing the dried gel to X-ray film. Proteins from 35S::bes1-GFP transgenic plants were used for phosphatase (CIP) treatments as described (Fankhauser et al., 1999).

Phosphatase Assay

The full-length BSU1 and phosphatase sequences were amplified from BSU1 cDNA with primers 5'-GTGAATTCGCTCCTGATCAATCTTATC-3' and 5'-GAGAATTCCATAAGAAGGTCATTTCGA-3' for the respective 5'-ends, and primer 5'-CGAGTCGACCCTTTATTCACTTGACTC-3' for the 3'-end. The fragments were cloned into the EcoRI/SalI sites of pMAL-C (New England Biolabs). Cultures of transformed *E. coli* BL21-CodonPlus-RIPL cells (Stratagene) were grown at 18° C. in YEP medium supplemented with 0.2% glucose and 1 mM MnCl$_2$ until they reached an OD$_{600}$ of 0.6, induced with 40 mM IPTG, and grown for an additional 10 h at the same temperature. The fusion proteins were purified and their phosphatase activity assayed according to the manufacturer's specifications (PSP Assay System; New England Biolabs). Inhibition studies were performed using similar procedures, adding okadaic acid (Sigma) or Inhibitor-2(New England Biolabs) to the reaction.

Shape Based in Silico Screening

A library of compounds against which to screen was assembled from compounds of almost 40 different vendors and comprised more than 7 million original compounds.

The program ROCS (Open Eye Scientific software, USA) was used to perform shape based virtual screening. The structure of abrasin was used as template against which the entire 3D-enumarated database of 11 million conformations was screened. For this purpose, the implicit Mills-Dean atom coloring scheme was used in conjunction with the standard shape-base matching of ROCS.

SPR Analysis

Biacore T100 was used to analyze interaction of abrasin with BIN2. Using amine coupling, purified GST-BIN2 was immobilized in the flow cell of a Series S CM5 Sensor Chip (Research Grade, Biacore AB). HBS-EP (Biacore AB) was used as running buffer, flow rate was set at 5 μl/min. The surface of the chip was activated by injecting a mixture of EDC (0.2 M) and NHS (0.05 M) for 10 min. Subsequently, 20 μg/ml GST-BIN2 in 10 mM sodium acetate buffer (pH 6.0) was injected for 20 min. The immobilization level of GST-BIN2 was≈20,000 RU. The chip was then flushed with 1 M ethanolamine (pH 8.5) for 10 min to deactivate the surface. A flow cell treated with a cycle of activation and deactivation without immobilized ligand was used as a reference.

Binding Experiments

Binding of abrasin to GST-BIN2 was performed in HBS-EP running buffer (Biacore AB) supplemented with 10 mM $MgCl_2$. abrasin was dissolved directly in running buffer at a concentration of 100 μM. Different concentrations of abrasin were injected at a flow rate of 30 μl/min over the reference and the GST-BIN2 flow cell for 90 s, followed by 180 s of buffer flow (dissociation phase). Zero concentration samples were used as blanks. The flow cell temperature was set to 25° C. Biacore T100 evaluation software (version 1.1.) was used for curve fitting, assuming a 1:1 binding model.

Microarray Analysis

Col-0 seeds were germinated vertically on ½ MS medium for 7 days under 16 h light/8 h dark cycles. The seedlings were overlaid with liquid ½ MS medium containing 1 μM brassinolide (BL, Fuji Chemical Industries, Ltd., Toyama, Japan), 30 μM abrasin (BIK, ChemBridge Corporation) and DMSO and treated for 30 and 120 min. The shoot parts were collected for RNA isolation. All sampling points were performed in three independent experiments. RNA was extracted using RNeasy kit (Qiagene). 200 μg total RNA per array was used to hybridise the ATH1 Affymetrix *Arabidopsis* arrays according to standard procedure. The overrepresentation analyses were performed using BiNGO software (Maere et al., 2005).

Plant Material and Treatments

Col-0, the null BR signaling bri1-116 (Friedrichsen et al., 2000) and BR biosynthetic cpd (Szekeres et al., 1996) mutants were subjected to phenotype rescue analysis by treatments with BL and ABRASIN. As a negative control, dimethylsulfoxide (DMSO) was used. Plants were germinated in vitro for 5 days on ½ MS containing DMSO medium and from day $6^{th}$ to day $11^{th}$ they were transferred on medium supplemented with BL (10 nM, 100 nM, 1000 nM), ABRASIN (5 μM, 10 μM, 30 μM) or DMSO. Cotyledons and leaves were collected for flowcytometric analysis at the $11^{th}$ day (i.e. 6 days of treatments). Samples for β-glucuronidase (GUS) assay were taken on day $6^{th}$ (i.e. 1 day treatments), $8^{th}$ (i.e. 3 days treatments), $10^{th}$ (i.e. 5 days treatments). Rescue of soil-grown mutants at different growth stages was checked by watering bri1-116 and cpd mutants with either BL or 2 ml 300 μM ABRASIN per day.

Flowcytometric Analysis of Leaves

Samples for flow cytometric analysis were collected and analyzed as described earlier (De Veylder et al., 2001)

GUS Assay

GUS staining was carried out by the method described by Jefferson et al. (1987). Images of GUS stained plants were taken with binocular microscope (MZ16, Leica) and Nikon camera.

Example 1

Identification of a Monocyclic Brassinosteroid Mimetic

Using a chemical genetics approach, a commercial 10.000 compound library was screened for molecules, which exert a brassinosteroid-like phenotype on young *Arabidopsis thaliana* seedlings, in order to further elucidate the BR-signalling pathway. One compound (4-[(5-bromo-2-pyridinyl) amino]-4-oxobutanoic acid), designated abrasin (in the figures indicated as I5 or BIK), was identified which strongly induced elongation of leaves, petioles and the hypocotyl in a dosage-dependent manner. Furthermore, root elongation and lateral root development was inhibited with an $EC_{50}$-value of 20 μM (FIG. 3). The chemical structure of this small molecule however showed no resemblance to the steroid-structure of known brassinosteroids (FIG. 4). Testing derivative molecules using SAR (Structure Activity Relationship)-data showed that altering the general structure of abrasin abolishes its activity, implying that the entire molecule is necessary for activity. Only minor changes, like brome to chlorine, were able to change the potency without losing activity.

Example 2

Abrasin is Bypassing the Bri-1 Brassinosteroid Receptor Mutation

Figure 5:
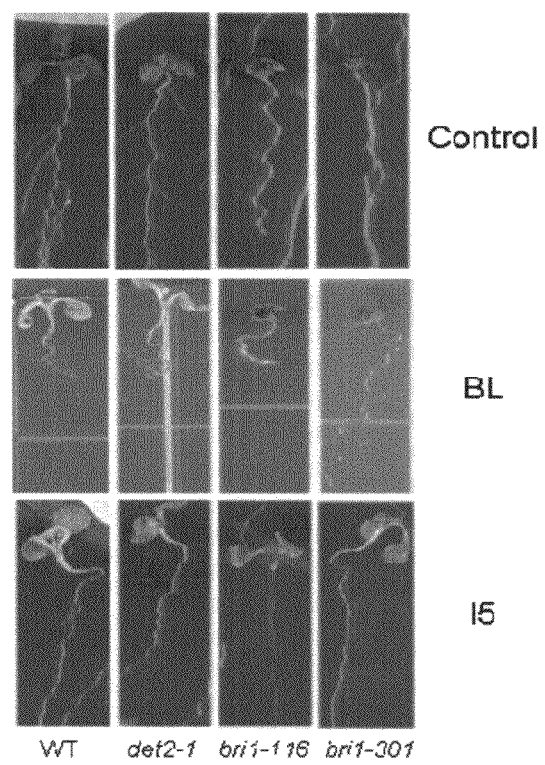
FIG. 5: Effect of brassinolide (BL) and abrasin (I5) treatment on mutants. WT or mutant plants were grown under standard conditions on agar plates. After 3 days of germination, plants were transferred to agar plates containing abrasin at a concentration of 50 µM or BL at a concentration of 1 µM.
Figure 6:
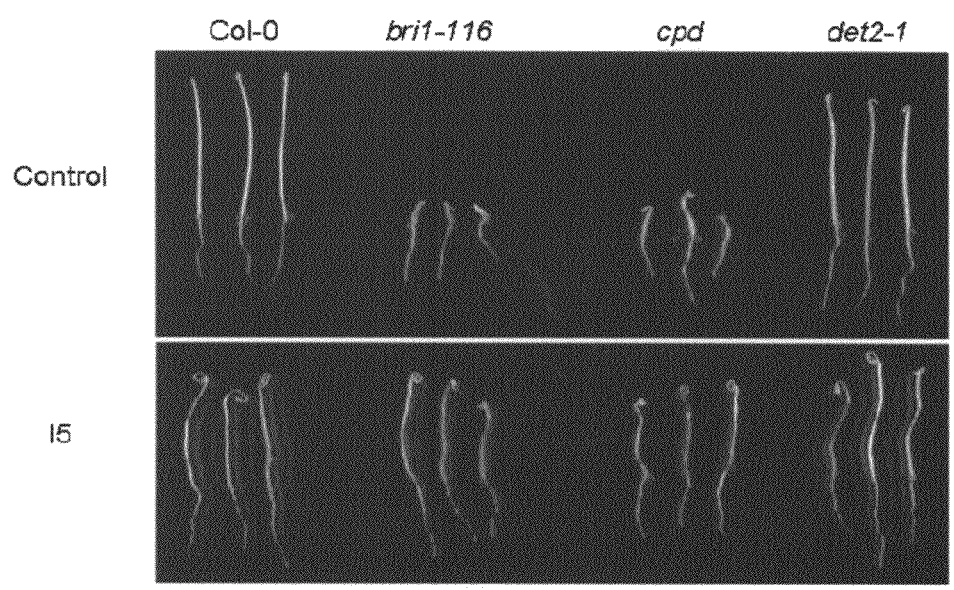
FIG. 6: Rescue of dark-grown BL mutants after treatment with 50 µM of abrasin (I5).
Figure 7:
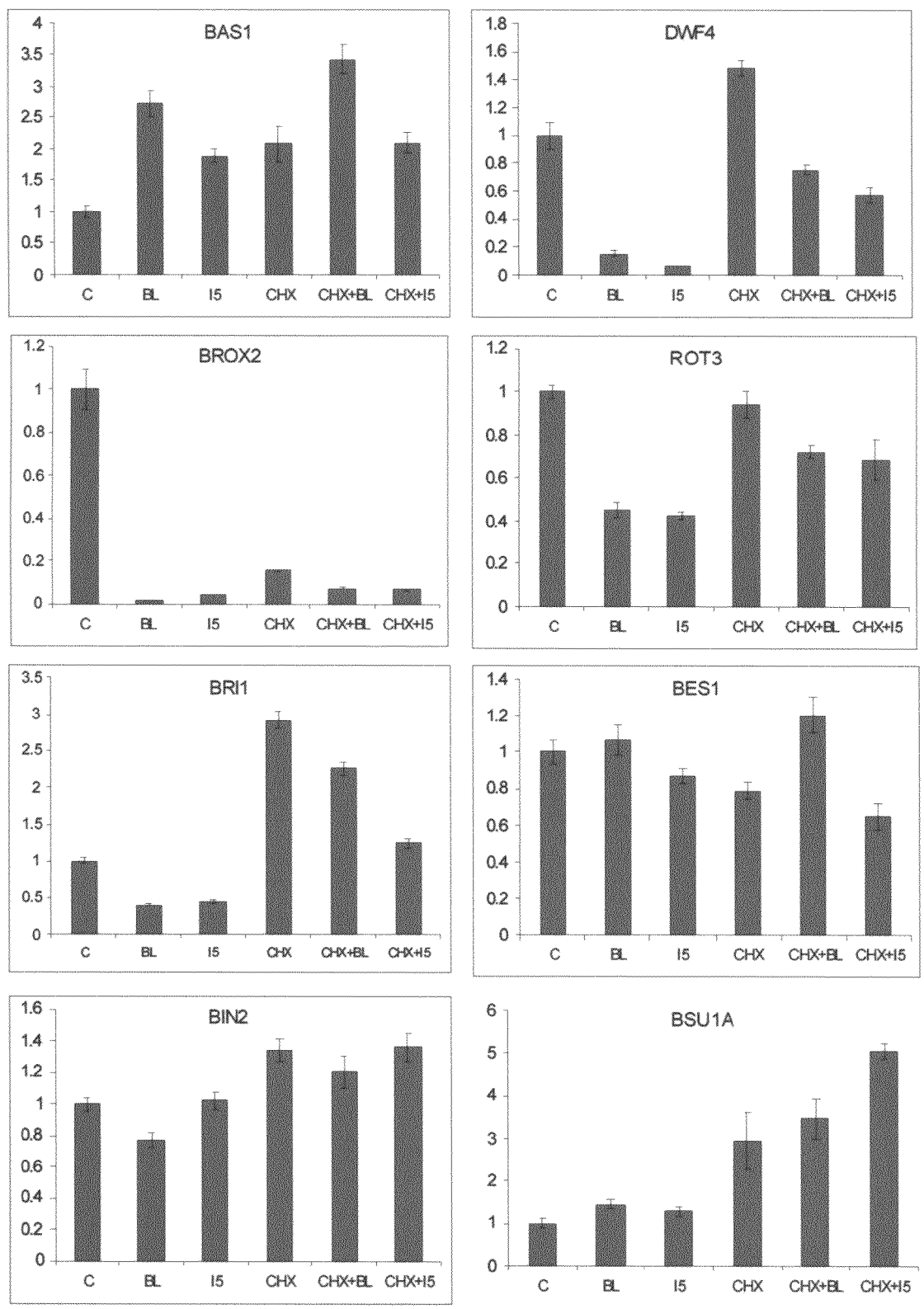
FIG. 7: Q-PCR analysis of genes involved in BR biosynthesis. WT *Arabidopsis* plants were treated with abrasin (indicated as I5) for 2 hours at a concentration of 30 µM and/or with CHX at a concentration of 30 µM and RNA was extracted from whole plants.
Figure 7:
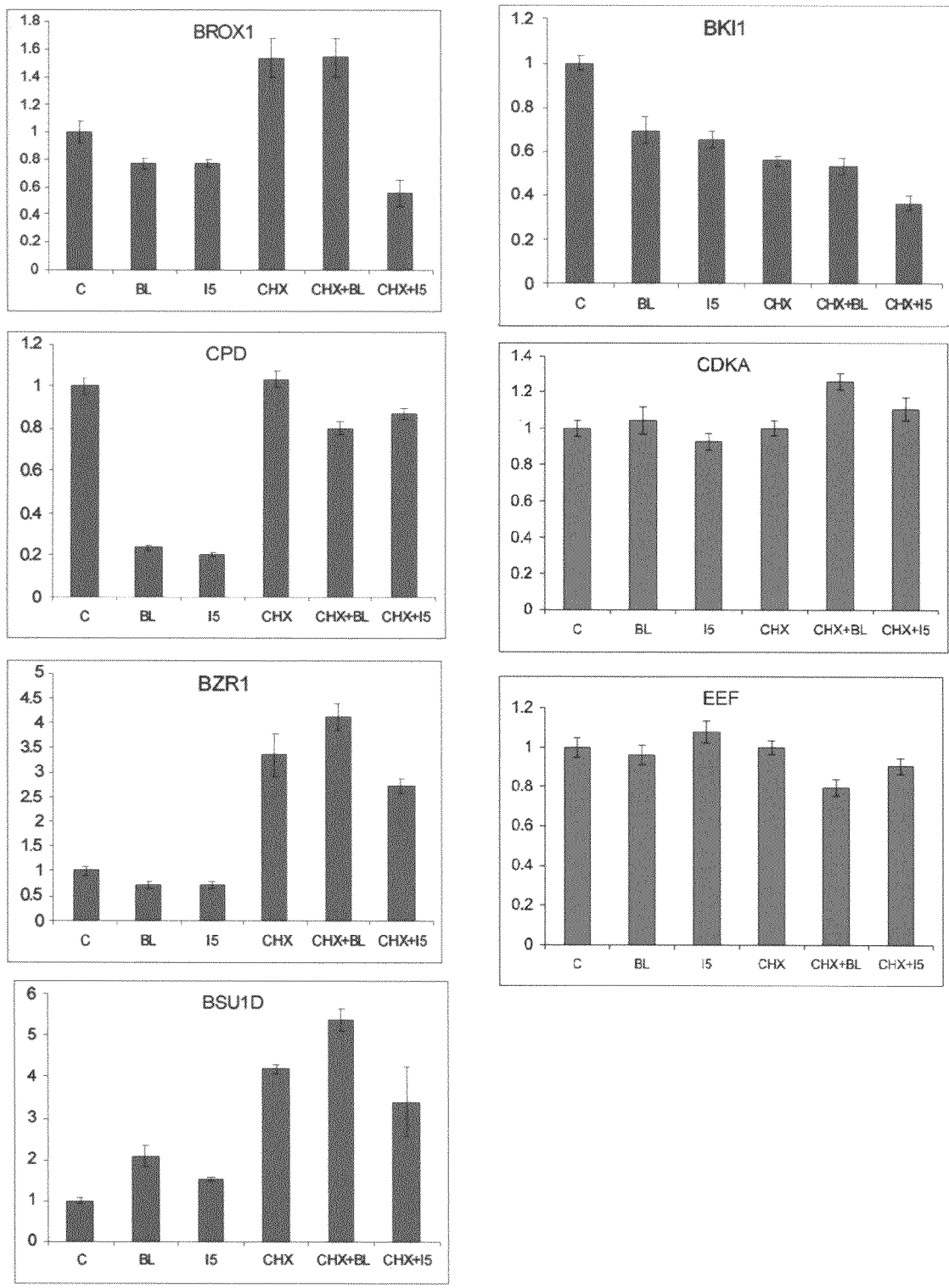

To determine whether the compound acts in the brassinosteroid signalling cascade, the effect on known brassinosteroid mutants was examined. Mutants in BR-biosynthesis (cdp, det2-1) and perception (bri1-116, bri1-301) are known to show a dwarfed phenotype. Addition of brassinolide (BL) rescues the cpd and det2-1 mutants, but not the bri1 receptor mutants. When grown on medium supplemented with abrasin all mutant lines, including the bri1 receptor mutants, showed an elongated phenotype (FIG. 5). Furthermore, when grown in the dark, the cpd, det2-1, bri1-116 and bri1-301 mutants have short hypocotyls compared to wild type plants. When grown in the dark on medium supplemented with the compound, all mutant lines had hypocotyls of normal length (FIG. 6). These data indicate that both light and dark-grown mutant phenotypes are completely rescued to wild type by abrasin. Taken together, these data suggest that the compound interferes rather with brassinosteroid signalling downstream of BRI1 than with biosynthesis or perception.

Example 3

Abrasin is Inducing the Brassinosteroid Signalling Cascade Downstream the Receptor Also at the transcriptional level, a number of significant changes are invoked by abrasin treatment. Downstream of the BRI1 receptor, all genes are upregulated, suggesting an activation of the pathway. Cycloheximide (CHX) was able to induce some of these genes, but the effect of BL or abrasin treatment was not altered, which implies that the effects of abrasin are primary responses. Furthermore, all genes involved in biosynthesis and perception are regulated in the same way as a BL-treatment, indicating that this is a secondary effect caused by the activation of the signalling cascade.

Figure 8:
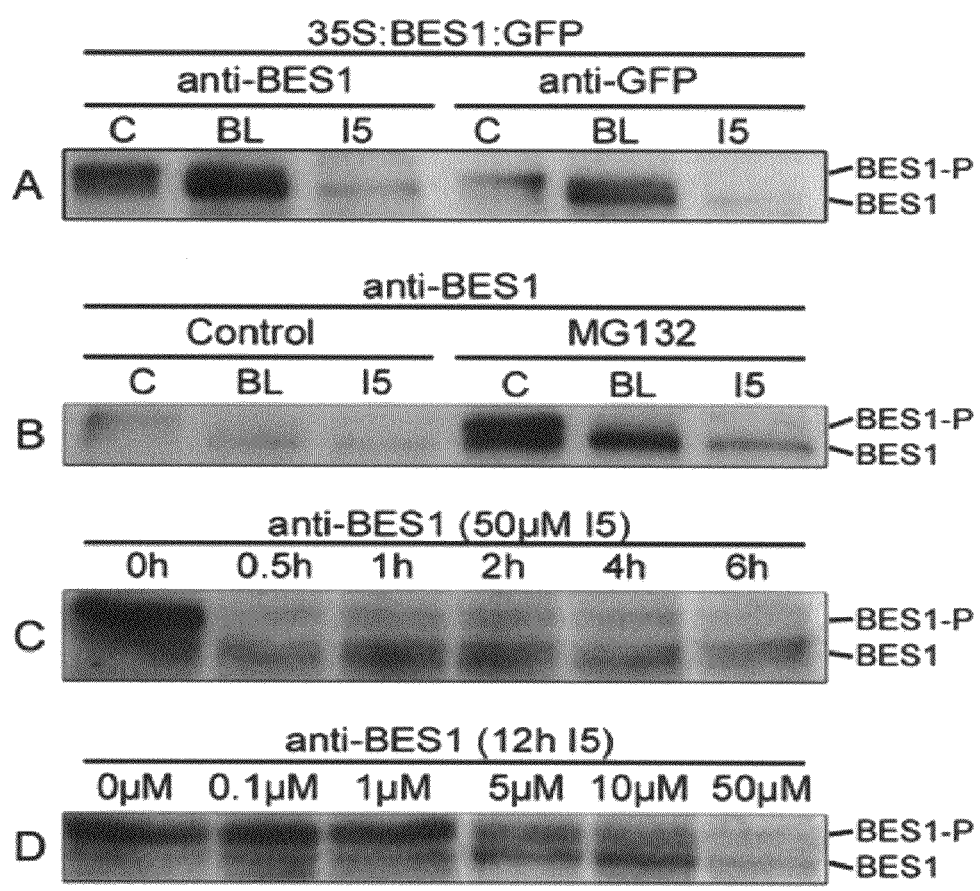
FIG. 8: A: Western Blot analysis of the BES1 protein in 35S:BES1:GFP plants treated with BL and abrasin (indicated as I5 throughout the figure) (A); MG132 with BL or abrasin (B); a time course with abrasin (C) and a concentration gradient with abrasin (D). B: Abrasin and BL induce similar transcriptional regulation of the BR pathway. Transcriptional regulation (relative expression levels) of five BR-biosynthetic genes (DWF4, CPD, ROT3, BR6OX1 and BR6OX2), five BR-regulated genes (BRI1, BIN2, BSU1, BES1 and BZR1) and two BR-upregulated genes (SAUR-AC1 and BAS1) on 3-day-old seedlings after treatment with BL (1 µM) or Abrasin (30 µM) for 6 hours compared to DMSO treated controls (all results are means±s.d.; individual reactions were performed in triplicate and experiments were repeated at least twice).
Figure 8B:
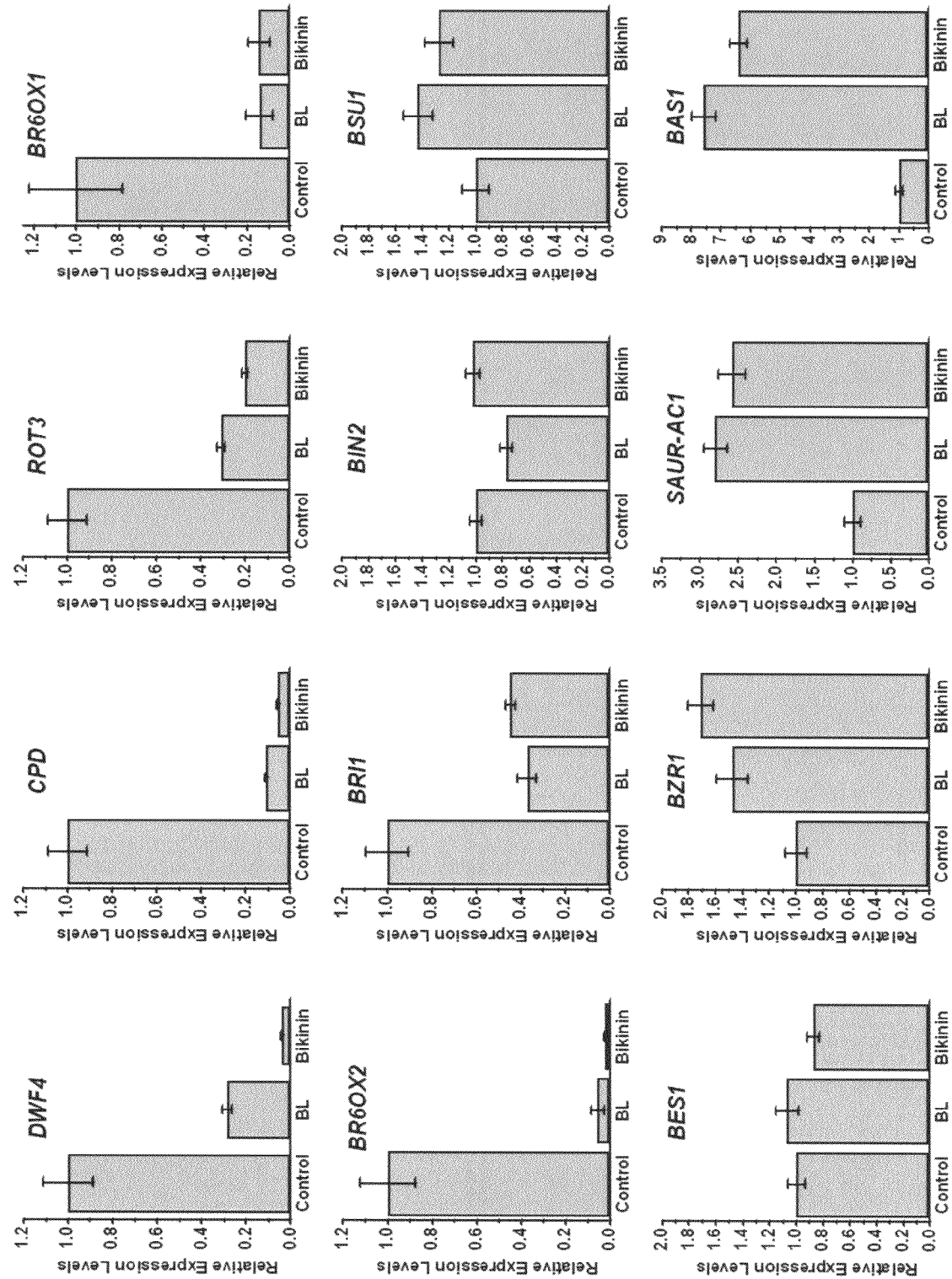

Downstream of BRI1, the nuclear BES1 protein plays a central role in a phosphorylation dependent mechanism. Recent evidence showed that phosphorylation by the BIN2 kinase leads to inhibition of the DNA-binding ability on the BR-responsive target promoters as well as inhibition of transcriptional activity through impaired multimerization. Dephosphorylation of BES1 by the serine/threonine phosphatase BSU1 on the other hand, induces the BR-response. Because of this important role of the BES1 phosphorylation state, the effect of abrasin was compared to that of a BL treatment (FIG. 8A). When grown on control medium, there is more phosphorylated BES1 protein present than its non-phosphorylated form. Addition of BL induces more non-phosphorylated protein. At low concentrations of abrasin of 5 to 10 µM, a shift towards non-phosphorylated BES1 is observed. At high concentrations of 50 µM however the total amount of BES1 protein is also reduced. Moreover, the observed shift towards the non-phosphorylated protein occurs very rapidly within 30 minutes after addition of abrasin to the medium. This correlates with the observation made before that the effect of abrasin is a primary response.

In its phosphorylated form, BES1 is thought to be degraded by the 26S proteasome. A treatment with the proteasome inhibitor MG132 however, revealed that when protein degradation is inhibited, no shift in the ratio between the phosphorylated and the dephosphorylated form is observed. However, there is an increase in the total amount of BES1. Our results support the recent view that this regulation of protein levels is not a primary response to BRs, nor a requirement for BR signalling. The reduction in protein level of BES1 is however also observed in bin2-1 mutants compared to wild type plants after BL treatment. This indicates that abrasin, like BL, specifically inhibits BIN2 but in an even stronger manner.

To determine whether abrasin induces the BL-type growth by controlling the same subset of BR target genes, we analyzed the effect of abrasin treatment on the RNA levels of BR feedback-regulated biosynthetic genes (DWF4—Choe at al 1998; CPD—Szekere et al., 1996, ROT3—Tanaka at al., 2005, BR6OX1—Shimada et al., 2003 and BR6OX2—Shimada et al., 2003), genes encoding BR signaling components (BRI1—Clouse et al, 1996, BIN2—Li and Nam, 2002; Li et al., 2001, BSU1—Mora-Gracia et al., 2004, BES1—Li and Deng, 2005 and BZR1—Li and Deng, 2005) and BR-induced genes (SAUR-AC1—Vert et al., 2005 and BAS1—Neff et al., 1999). For all genes, the expression profiles resembled closely those of BL treatment (FIG. 8 B), indicating that abrasin promotes a growth response harboring a BL signature through a common transcriptional growth-regulatory module.

Example 4

Figure 10:
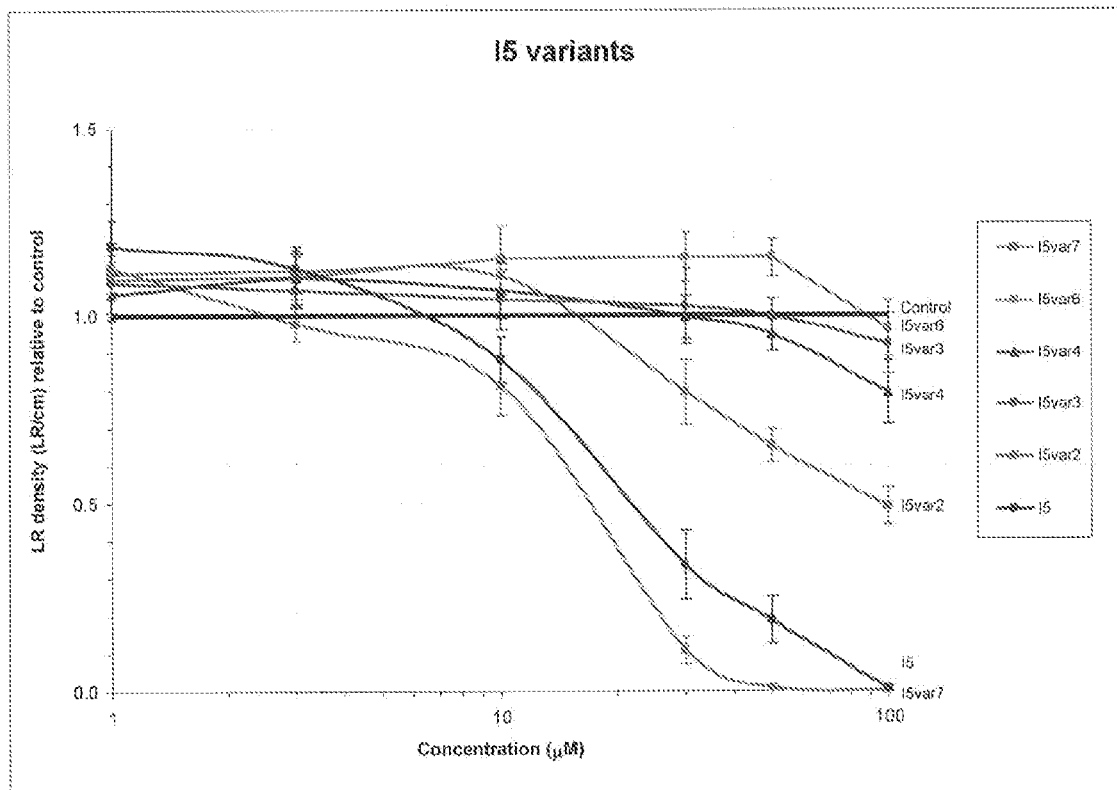
FIG. 10: Effect on lateral root density of abrasin (indicated as I5) derivatives. Error bars represent standard error of the mean.

Structure-Function Analysis of Abrasin; Isolation of Alternative Monocyclic Brassinosteroid Mimetics Several structural variant of abrasin were tested on their effect on the lateral root formation, as an indication of their brassinosteroid like activity. The compounds are listed in FIG. 9. All tested derivatives have completely abolished the activity, except variant 2 and variant 7 (FIG. 10). Halogenation of the ring structure seems to be critical for the function; the activity is decreasing in the series F—Cl—Br—I, with the highest activity for the fluoro derivative. The nitrogen in the aromatic ring contributes to some extent to the activity.

Example 5

In Silico Derivation of Alternative Brassinosteroid Mimetics

Based on the structure of abrasin, using a shaped based screening, several alternative compounds with potential brassinosteroid mimetic activity were derived (FIG. 11)

Example 6

Abrasin Inhibits BIN2 Kinase Activity

Figure 12:
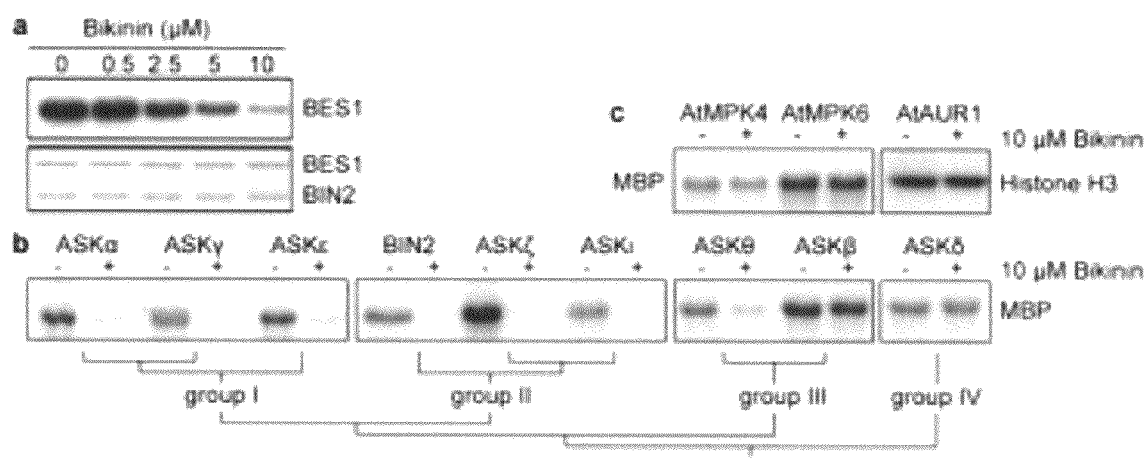
FIG. 12: Abrasin specifically inhibits kinase activity of BIN2 and other GSK-3-like kinases in plants. a, Autoradiography of a kinase assay with GST-BIN2 and MBP-BES1 on a concentration range of 0 to 10 µM abrasin. Coomassie staining was used as a loading control. b, Autoradiography of kinase assays with nine ASKs with MBP as a substrate in the presence or absence of 10 µM abrasin. The second member of group IV, ASKκ, had no kinase activity and was not included in the analysis. c, Autoradiography of kinase assays with AtMPK4, AtMPK6 and MBP as a substrate (left) and with AtAUR1 kinase and histone H3 as a substrate (right) in the presence or absence of 10 µM abrasin.

We next examined whether abrasin interferes with the activity of the BIN2 kinase by performing in vitro kinase assays. Abrasin strongly reduced BIN2 kinase activity towards its substrate BES1 in a dose-dependent manner (FIG. 12a). The inhibitory effect of abrasin was already apparent at concentrations lower than 2.5 µM and was dramatic at 10 µM. To demonstrate that abrasin interacts directly with BIN2, we performed surface plasmon resonance (SPR) experiments. GST-BIN2 was immobilized on a sensor chip via amine coupling and increasing concentrations of abrasin were injected over the sensor surface.

Figure 13:
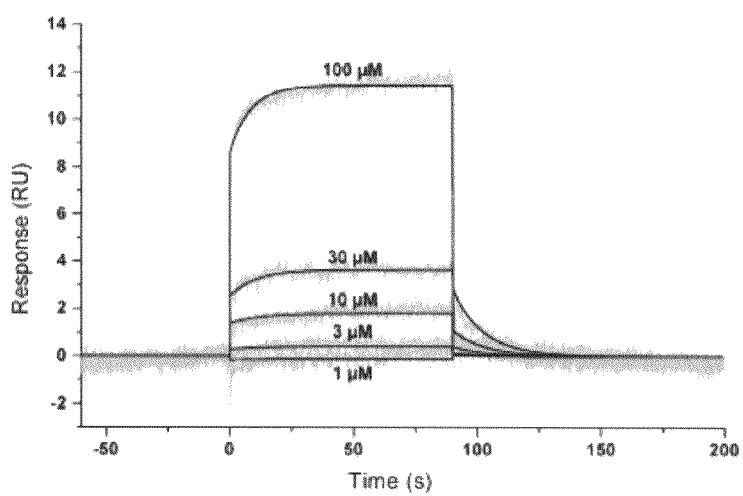
FIG. 13: Abrasin directly interacts with BIN2. SPR sensorgrams for abrasin binding to GST-BIN2 after injection of different abrasin concentrations as indicated. The binding curves are overlaid by calculated curves resulting from the global fits of the data to a 1:1 interaction model ($\chi^2$=0.126). The kinetic parameters obtained for the interaction are $k_a$=407 $M^{-1}s^{-1}$, $k_d$=0.081 $s^{-1}$, $K_D$=199 µM. Reference and blank data are subtracted. The experiment was performed in triplicate.

Abrasin interacted with immobilized GST-BIN2 in a dose-dependent manner (FIG. 13), with a clear response starting from a concentration of 10 µM. In summary, these observations combined with expression and mutant analyses allow us to conclude that BIN2 represents a direct target of abrasin.

Besides BIN2, nine additional GSK-3 kinases (also designated ASKs for *Arabidopsis* SHAGGY-related kinases) divided into four subgroups (I-IV) have been identified in *Arabidopsis* (Jonak and Hirt, 2002; Yoo et al. 2006). To determine the specificity of abrasin, its effect on the kinase activity of all ASKs was analyzed with myelin basic protein (MBP) as a general substrate. Abrasin strongly inhibited the activity of the closely related groups I and II (FIG. 12b) with some residual activity (6-8%) for group I kinases and total inhibition (1-2 residual activity) for members of group II including BIN2. Surprisingly, one member of group III, ASKθ, was moderately inhibited (20% residual activity), whereas the activity of the other member, ASKβ, was not affected by abrasin. The major difference in protein sequence between ASKθ and ASKβ is localized at the N- and C-terminus (Jonak and Hirt, 2002), suggesting that N- or C-terminal residues might be crucial in determining the specificity of abrasin. Furthermore, abrasin had no effect on the activity of three unrelated *Arabidopsis* Ser/Thr kinases (AtMPK4, AtMPK6 and AtAUR1; FIG. 12c). These data indicate that the activity of abrasin is GSK-3 specific with additional specificity for certain subgroups. Currently, only members of group II GSK-3 kinases have been shown to be implicated in BR signaling (Vert and Chory, 2006, Jonak and Hirt, 2002). Interestingly, abrasin also inhibits the kinase activity of group I and ASKθ in vitro. However, it still remains to be demonstrated that these ASKs play a role in BR signaling besides the members of group II.

Example 7

Microarray Analysis after Brassinolide or Abrasin Treatment

We performed a microarray analysis using the *Arabidopsis* whole genome chip (Affymetix) to determine whether abrasin activated the expression of BR-inducible genes at transcriptional level. Wild-type Col-0 seedlings were exposed to 1 µM BL, 30 µM ABRASIN and DMSO (mock-treatment) for two time points (30 min and 120 min) and the shoot parts were collected for RNA isolation. The analysis of the variance of the normalized gene expression data took in account the variability parameters affecting the expression level: type of hormone treatment, duration of treatment and the interaction between these two. Of the nearly 23000 genes on the chip, 272 genes gave signals that were significantly above the background level in all samples at a high stringency mode (p-value of 0.05 and minimal fold change 2). Next, a subset of well-represented Gene Ontology (GO) terms (BiNGO) was used to identify functional trends in the 272 responsive genes. This analysis showed that genes encoding proteins involved in BR metabolism, BR biosynthesis, hormone mediated signaling and transcription were significantly enriched consistent with the role of BL and ABRASIN in BR signal transudation cascade. Interestingly genes expressed in response to auxin and abiotic stimuli were also overrepresented.

Figure 14:
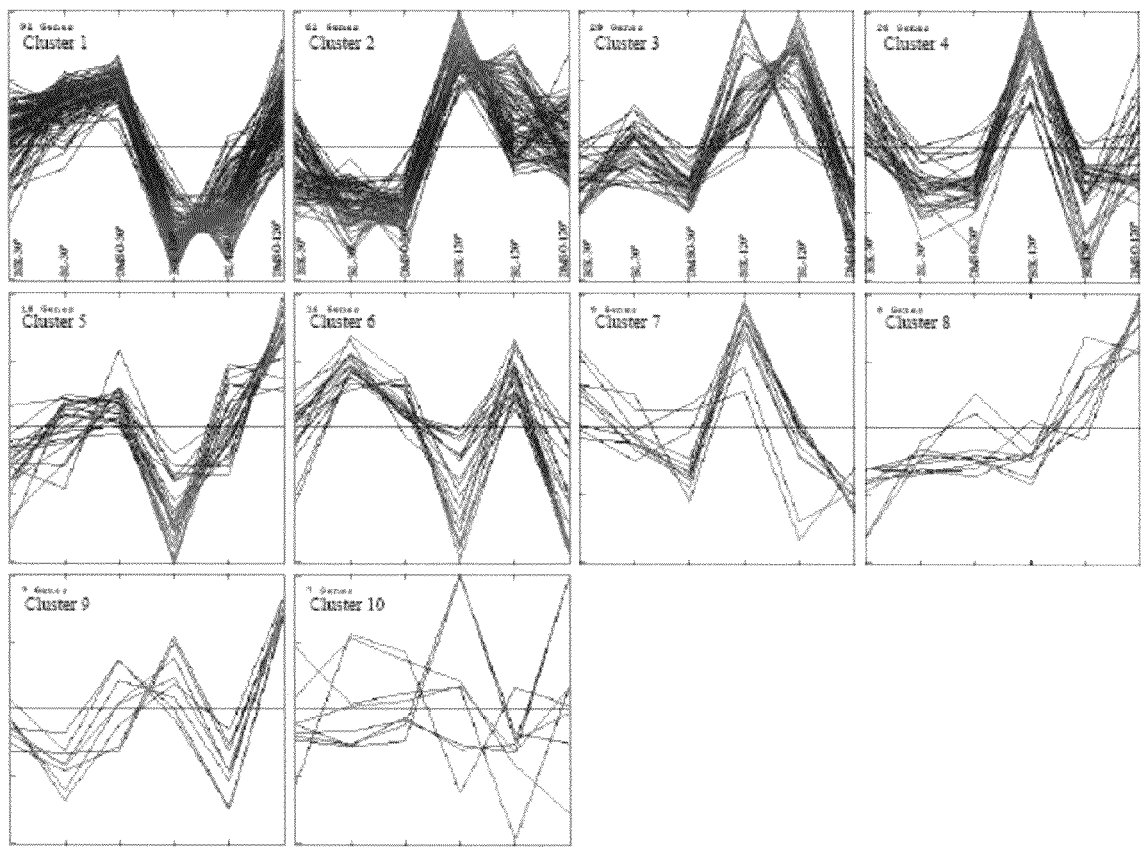
FIG. 14: Clustering of gene expression profiles by QT-clust analysis. Clusters illustrating the major patterns of the data sets. Points: BIK-30: 30 µM abrasin 30 min; BL-30: 1 µM brassinolide 30 min; DMSO-30: control DMSO 30 min; BIK-120: 30 µM abrasin 120 min; BL-120: 1 µM brassinolide 120 min; DMSO-120: control DMSO 120 min. Cluster 1: 92 genes; Cluster 2: 62 genes; Cluster 3: 28 genes; Cluster 4: 26 genes; Cluster 5: 18 genes; Cluster 6: 16 genes; Cluster 7: 9 genes; Cluster 8: 8 genes; Cluster 9: 7 genes; Cluster 10: 7 genes.

Quality threshold (QC) clustering divided the significantly modulated genes into 9 clusters containing genes that shared similar expression patterns and cluster 10 containing the remaining genes (FIG. 14, Table 1). The largest Cluster 1 (Table 1) contained 92 genes that were specifically and faster, within 30 min down-regulated by both BL and ABRASIN but somehow strongly affected by ABRASIN. 30% of those genes were previously reported to be down-regulated by BL in the global microarray analysis performed by Nemhauser et al., (2006). Consistent with the negative feedback regulation model of BR biosynthesis (Mathur et al., 1998), the expression of BR biosynthesis genes (CPD, DWF4, BR6OX2) was down-regulated in Cluster 1. Both ABRASIN and BL treatment significantly down-regulated genes involved in the auxin pathway e.g. PINT, IAA29 and IAA2 as previously reported (Mussig et al., 2002; Goda et al., 2002, 2004).

In Cluster 3 (Table 1), 28 genes were found to be up-regulated early by BL and later by ABRASIN. This cluster was enriched in genes previously referred to as early auxin-inducible genes from the SAUR family (SAUR-AC1, SAUR14, SAUR10 and SAUR16). Interestingly those genes were induced by BL as faster as 30 min treatment whether ABRASIN had an effect only after 2 hours. This is consistent with previous microarray studies showing that BL indices the expression of the auxin inducible SAUR, GH3 and IAA gene families, (Goda et al., 2004, Nemhouser et al., 2004, 2006) in a period of 30 to 60 min.

Cluster 2 (Table 1) was enriched in genes mainly early up-regulated by the ABRASIN. However from those genes 70% were up-regulated and 30% not affected or even down-regulated later by the BL treatment. In Cluster 4 (Table 1) 26 genes were up-regulated by ABRASIN but either not changed or slightly down-regulated by BL. Based on the general expression patterns we can assume that Clusters 2 and 4 are enriched in ABRASIN up-regulated genes. ABRASIN but not BL induces the expression of 4 WRKY-family of transcription factors (WRKY15, WRKY53, WRKY33 and WRKY6), 3 DOF-type zing finger domains containing proteins (At5g60200, At2g37590, At2g28510) 2 lectin receptor-like kinases (At4g02410, At5g60270), 2 U-box domain containing proteins (At1g66160, At3g49810) and previously described HAESA (Jinn et al., 2000) and HAESA-like (At5g25930) LRR-type receptor-like kinases. *Arabidopsis* WRKY proteins comprise a family of plant specific zinc-finger-type transcription factors involved in the regulation of gene expression during pathogen defense, wounding and senescence (Eulgem and Somssich, 2007). In addition to regulating the expression of defense-related genes, WRKY transcription factors have also been shown to regulate cross-talk between jasmonate- and salicylate-regulated disease response pathways (Li et al., 2004). Dof proteins are members of a major family of plant transcription factors associated with plant-specific phenomena including light, phytohormone and defense responses, seed development and germination (Yanagisawa, 2002). Function of HAESA was also implicated in floral organ abscission (Jinn et al., 2000). Although BRs were recently implicated in plant immunity and cell death (Kemmerling et al., 2007; Chinchilla et al., 2007), none of the ABRASIN specific proteins was shown to function in BR depended fashion. Cluster 5 (Table 1) was enriched in genes fast down-regulated by ABRASIN from witch around 50% were later affected by BL. To some extend this cluster overlapped with Cluster 1. ABRASIN specific responses (Clusters 2, 4 and 5) were anticipated based on the observations that ABRASIN was able to inhibit the activity of not only BR specific group II GSKs in *Arabidopsis* but also group I GSKs and one member of group III.

Interestingly, Cluster 6 (FIG. 14; Table 1) contained genes that were fast up-regulated by BL whether ABRASIN treatment affected them both very weekly and late or had an opposite effect. This cluster was significantly enriched in early auxin-responsive genes from the SAUR family similarly to Cluster 3 and genes involved in stomata patterning and differentiation (Nadeau and Sack, 2002; Hara et al., 2007). Whereas BL initiated the expression of the auxin inducible genes with in 30 min consistent with previous reports (Goda et al., 2002, 2004), ABRASIN had only later and less strong effect on them. Recently a synergistic interaction between the brassinosteroid and auxin pathways was suggested based on shared target genes from their microarray data In addition a model was proposed were both pathways converge at the level of transcriptional regulation of target genes with common regulatory elements (Nemhauser et al., 2004). Our observations however suggest that the transcriptional initiation of auxin genes was not solely a result of the inhibition of BIN2 and BIN2-like GSKs. Whereas the activation of auxin responsive genes was dependent on BRI1, direct BIN2 inhibition did not result in fast auxin responses suggesting that auxin responses are result of yet unknown, BIN2 independent pathway. Interestingly, ABRASIN was able to initiate auxin responses later possibly by affecting the negative feedback loop on the BR biosynthesis. Clusters 7, 8 and 9 covered genes with more complex expression patterns.

Example 8

Figure 15:
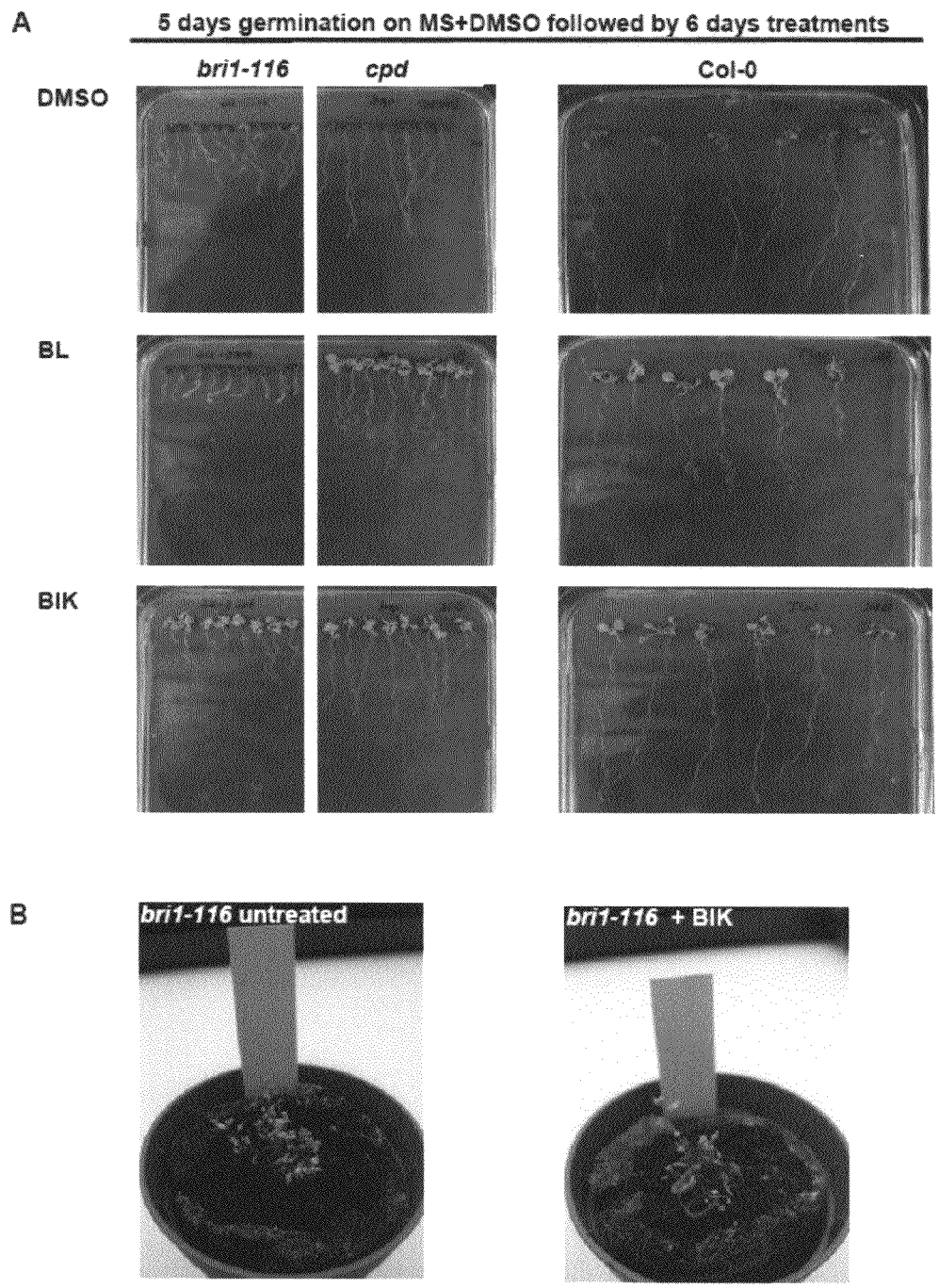
FIG. 15: Phenotype rescue of bri1-116 and cpd mutants. (A.) The mutant and Col-0 plants were germinated on MS+DMSO medium till day 5 and afterwards transferred on MS supplemented with DMSO, 1 µM BL or 30 µM ABRASIN until day 11. Treatment with BL rescues the cpd mutant phenotype but not bri1-116 while ABRASIN rescues both mutants. (B.) 1 month-old bri1-116 plants grown in soil were watered each day with 2 ml 300 µM ABRASIN solution which suggests ABRASIN uptake through the root. Visible elongation of the stem and petioles was observed in one week. BL: brassinolide; BIK: abrasin.

ABRASIN Rescue Experiments bri1-116 null mutant (Friedrichsen et al., 2000) is deficient for the BR receptor, BRASSINOSTEROID INSENSITIVE 1 (BRI1) resulting in severe dwarf phenotype similar to the BR-biosynthetic null mutant, cpd (Szekeres et al., 1996). While brassinolide (BL), the most potent BR rescued the dwarf statute of the cpd to a wild-type, bri1-116 was insensitive and therefore unaffected by BL Further we followed the effect of ABRASIN on BR mutants. bri1-116, cpd and Col-0 plants were grown in vitro for 5 days so the mutant phenotype was distinguishable from the wild-type (both mutants were maintained in hemyzygous state). The homozygous mutants and the wild-type were then transferred to % MS medium containing 1 µM BL or 30 µM ABRASIN and further grown for another 6 days. Treatment with ABRASIN rescued the phenotypes of both bri1-116 and cpd mutants to the wild-type (FIG. 15). Phenotypic changes were observed 1 day after the treatment (day 6) and the effect increased within the next days (day 11, FIG. 15A).

We next aimed to rescue soil-grown mutants, bri1-116 and cpd by watering them with either BL or ABRASIN solutions at different growth stages. In trial experiments bri1-116 and cpd mutants were watered with 2 ml 300 µM ABRASIN per day. This treatment was sufficient to slightly change the phenotype of 1 month-old bri1-116 plants in a week (FIG. 15B). These results showed that ABRASIN can rescue both BR perception and biosynthesis mutants.

Example 9

ABRASIN Rescues the Leaf Growth Defects in bri1-116 and cpd by Inducing Cell Proliferation We further investigated what are the cellular bases of the ABRASIN effect and if the mechanism by which ABRASIN and BL rescued the BR mutants was the same. We first tested different ranges of BL and ABRASIN concentrations in in vitro growth experiments on bri1-116 and cpd mutants At the 11 day, i.e. 6 days of treatments, the results were compared. It was demonstrated that 10 nM BL and 10 µM ABRASIN were sufficient to rescue the mutant phenotypes (FIG. 16). In parallel cotyledons and leaves form bri1-116 and cpd mutants were collected following each treatment and analyzed for DNA content by flowcytometry. The data demonstrated that ABRASIN treatment significantly increased the 2C and 4C content and completely suppressed the 16C content even at low concentrations for both bri1-116 and cpd leaves. These results might suggest that ABRASIN increases the cell division activity in the treated leaves (FIGS. 16A and B). Interestingly ABRASIN had effect only on leaves as the values for cotyledons did not differ form the untreated controls. Although BL treatment rescued the cpd leaves it did not significantly changes the DNA content distribution (FIG. 16C).

To examine what are the molecular bases of the different ABRASIN and BL effects, cell division (CYCB1; 1, CDKB1; 1) and auxin response (DR5) markers were introduced into bri1-116 and cpd mutants and compared with the wild-type. The activation of the markers was detected by localization of the activity of their promoters fused to β-glucuronidase (GUS) reporter gene in the leaf 1 and 2 (FIG. 5). Samples for GUS assay were taken at day $6^{th}$ (i.e. 1 day treatment), $8^{th}$ (i.e. 3 days treatment), and $10^{th}$ (i.e. 5 days treatment). The cell division marker, CYCB1; 1 was highly expressed in young leaves reflecting active cell proliferation (FIGS. 17A and B). In all cases ABRASIN treatment increased the CYCB1; 1 expression. CDKB1; 1 was used as a dual marker as its expression marked not only dividing cells but also differentiated guard cells and stomatal precursor cells (Boudolf et al., 2004). Treatment with ABRASIN activated CDKB1; 1-GUS predominately in the leaf vasculature whereas treatment with BL induced only stomata specific expression (see days 8 and 10, FIGS. 17A and B).

These results support the observation that ABRASIN induced strong cell division activity while the effect of BL was more related to cell differentiation.

Auxin response genes were induced by both ABRASIN and BL treatments and auxin has been implicated in leaf development (Mattsson et al., 2003; Scarpella et al., 2006). We next examined the auxin distribution in early leaf primordial bri1-116 and cpd mutants and the ability of the synthetic auxin inducible promoter DR5 to respond to ABRASIN and BL treatment. In bri1-116 leaves the auxin levels seemed to be lower which was previously shown for weaker bri mutants (Bao et al., 2004). 1 day of ABRASIN treatment did not significantly increases the DR5 activity in the leaves but the auxin levels in both bri1-116 and wild type leaves were increased after longer treatment (FIG. 17A). This preliminary observation suggested that cell division activity cause by the ABRASIN treatment is not a solely result of an enhanced auxin responses.

TABLE 1

Fold-change of genes following exposure to BL and ABRASIN (BIK) treatment.

| | | | | 30 min | | 120 min | |
|---|---|---|---|---|---|---|---|
| Cluster | Affymetrix no. | Accession no. | Annotation | BIK | BL | BIK | BL |
| 1 | 260655_at | AT1G19320 | pathogenesis-related thaumatin family protein | 0.52 | 0.81 | 0.50 | 0.38 |
| 1 | 258100_at | AT3G23550 | MATE efflux family protein | 0.67 | 0.84 | 0.38 | 0.31 |
| 1 | 250752_at | AT5G05690 | cytochrome P450 90A1 (CYP90A1) (CYP90) (CPD) | 0.63 | 0.93 | 0.29 | 0.41 |
| 1 | 247478_at | AT5G62360 | invertase/pectin methylesterase inhibitor family protein | 0.52 | 0.92 | 0.25 | 0.45 |
| 1 | 255942_at | AT1G22360 | UDP-glucoronosyl/UDP-glucosyl transferase family protein | 0.82 | 0.94 | 0.32 | 0.29 |
| 1 | 259373_at | AT1G69160 | expressed protein | 0.67 | 1.06 | 0.33 | 0.59 |
| 1 | 246580_at | AT1G31770 | ABC transporter family protein | 0.91 | 0.99 | 0.50 | 0.64 |
| 1 | 246735_at | AT5G27670 | histone H2A | 0.79 | 0.86 | 0.41 | 0.50 |
| 1 | 253812_at | AT4G28240 | wound-responsive protein-related | 0.49 | 0.77 | 0.33 | 0.41 |
| 1 | 262830_at | AT1G14700 | purple acid phosphatase | 0.53 | 0.73 | 0.47 | 0.59 |
| 1 | 259683_at | AT1G63050 | membrane bound O-acyl transferase (MBOAT) family protein | 0.75 | 0.98 | 0.27 | 0.40 |
| 1 | 264900_at | AT1G23080 | auxin efflux carrier protein (PIN7) | 0.81 | 0.89 | 0.33 | 0.48 |
| 1 | 251321_at | AT3G61460 | zinc finger (C3HC4-type RING finger) family protein (BRH1) | 0.43 | 0.78 | 0.32 | 0.43 |
| 1 | 252178_at | AT3G50750 | brassinosteroid signalling positive regulator-related (BEH1) | 0.63 | 0.99 | 0.31 | 0.35 |
| 1 | 250327_at | AT5G12050 | expressed protein | 0.52 | 0.73 | 0.27 | 0.34 |
| 1 | 261400_at | AT1G79630 | protein phosphatase 2C family protein | 0.62 | 0.78 | 0.35 | 0.37 |
| 1 | 261292_at | AT1G36940 | expressed protein | 0.45 | 0.89 | 0.32 | 0.38 |
| 1 | 254810_at | AT4G12390 | invertase/pectin methylesterase inhibitor family protein | 0.75 | 0.96 | 0.44 | 0.66 |
| 1 | 247191_at | AT5G65310 | homeobox-leucine zipper protein 5 (HB-5)/HD-ZIP transcription factor 5 | 0.90 | 0.91 | 0.20 | 0.27 |
| 1 | 262500_at | AT1G21760 | F-box family protein | 0.76 | 1.02 | 0.46 | 0.60 |
| 1 | 245987_at | AT5G13180 | no apical meristem (NAM) family protein | 0.77 | 1.07 | 0.39 | 0.50 |
| 1 | 250569_at | AT5G08130 | basic helix-loop-helix (bHLH) family protein (BIM2) | 0.76 | 0.79 | 0.37 | 0.42 |
| 1 | 250248_at | AT5G13740 | sugar transporter family protein | 0.81 | 0.77 | 0.23 | 0.36 |
| 1 | 262951_at | AT1G75500 | nodulin MtN21 family protein | 0.67 | 0.91 | 0.37 | 0.56 |
| 1 | 245761_at | AT1G66890 | expressed protein | 0.65 | 0.72 | 0.14 | 0.34 |

TABLE 1-continued

Fold-change of genes following exposure to BL and ABRASIN (BIK) treatment.

| Cluster | Affymetrix no. | Accession no. | Annotation | 30 min BIK | 30 min BL | 120 min BIK | 120 min BL |
|---|---|---|---|---|---|---|---|
| 1 | 245362_at | AT4G17460 | homeobox-leucine zipper protein 1 (HAT1)/HD-ZIP protein 1 | 0.29 | 0.54 | 0.11 | 0.19 |
| 1 | 247077_at | AT5G66420 | expressed protein | 0.92 | 1.04 | 0.42 | 0.43 |
| 1 | 259596_at | AT1G28130 | encodes an IAA-amido synthase | 0.64 | 0.85 | 0.40 | 0.28 |
| 1 | 266363_at | AT2G41250 | haloacid dehalogenase-like hydrolase family protein | 0.82 | 0.91 | 0.33 | 0.44 |
| 1 | 253662_at | AT4G30080 | transcriptional factor B3 family protein | 0.89 | 0.94 | 0.41 | 0.49 |
| 1 | 253062_at | AT4G37590 | phototropic-responsive NPH3 family protein | 1.04 | 0.90 | 0.43 | 0.53 |
| 1 | 253351_at | AT4G33700 | CBS domain-containing protein | 0.73 | 0.81 | 0.38 | 0.51 |
| 1 | 259848_at | AT1G72180 | leucine-rich repeat transmembrane protein kinase | 0.54 | 0.87 | 0.11 | 0.22 |
| 1 | 265511_at | AT2G05540 | glycine-rich protein | 0.71 | 0.92 | 0.54 | 0.46 |
| 1 | 253423_at | AT4G32280 | auxin-responsive AUX/IAA family protein (IAA29) | 0.32 | 0.66 | 0.13 | 0.22 |
| 1 | 256598_at | AT3G30180 | cytochrome p450 enzyme | 0.09 | 0.31 | 0.06 | 0.07 |
| 1 | 267628_at | AT2G42280 | basic helix-loop-helix (bHLH) family protein | 0.67 | 0.98 | 0.28 | 0.41 |
| 1 | 265245_at | AT2G43060 | expressed protein, similar to cDNA bHLH transcription factor | 0.31 | 0.25 | 0.25 | 0.36 |
| 1 | 245319_at | AT4G16146 | expressed protein | 0.91 | 0.82 | 0.49 | 0.55 |
| 1 | 245784_at | AT1G32190 | expressed protein | 0.73 | 1.00 | 0.07 | 0.11 |
| 1 | 253751_at | AT4G29070 | expressed protein | 0.78 | 0.90 | 0.50 | 0.74 |
| 1 | 262635_at | AT1G06570 | 4-hydroxyphenylpyruvate dioxygenase (HPD | 0.91 | 0.87 | 0.29 | 0.27 |
| 1 | 252890_at | AT4G39400 | brassinosteroid insensitive 1 (BRI1) | 0.71 | 0.96 | 0.46 | 0.57 |
| 1 | 247880_at | AT5G57780 | expressed protein | 0.35 | 0.41 | 0.13 | 0.12 |
| 1 | 246284_at | AT4G36780 | brassinosteroid signalling positive regulator-related | 0.49 | 0.71 | 0.03 | 0.09 |
| 1 | 266591_at | AT2G46225 | Encodes a subunit of the WAVE complex | 1.15 | 0.97 | 0.58 | 0.47 |
| 1 | 257374_at | AT2G43280 | far-red impaired responsive family protein | 0.78 | 0.84 | 0.48 | 0.51 |
| 1 | 257766_at | AT3G23030 | auxin-responsive protein/indoleacetic acid-induced protein 2 (IAA2) | 0.55 | 0.66 | 0.25 | 0.39 |
| 1 | 261456_at | AT1G21050 | expressed protein | 0.32 | 0.72 | 0.14 | 0.22 |
| 1 | 257855_at | AT3G13040 | myb family transcription factor | 0.93 | 0.84 | 0.48 | 0.54 |
| 1 | 256960_at | AT3G13510 | expressed protein | 0.85 | 1.06 | 0.42 | 0.83 |
| 1 | 253247_at | AT4G34610 | homeodomain-containing protein | 1.02 | 0.86 | 0.41 | 0.37 |
| 1 | 267305_at | AT2G30070 | potassium transporter (KUP1) | 0.61 | 0.81 | 0.22 | 0.38 |
| 1 | 245075_at | AT2G23180 | cytochrome P450, putative | 0.67 | 1.10 | 0.36 | 0.42 |
| 1 | 257858_at | AT3G12920 | expressed protein | 0.45 | 0.81 | 0.31 | 0.41 |
| 1 | 252184_at | AT3G50660 | steroid 22-alpha-hydroxylase (CYP90B1) (DWF4) | 0.47 | 0.47 | 0.02 | 0.02 |
| 1 | 263002_at | AT1G54200 | expressed protein | 1.26 | 1.16 | 2.19 | 2.06 |
| 1 | 257642_at | AT3G25710 | basic helix-loop-helix (bHLH) family protein | 0.48 | 1.06 | 0.10 | 0.53 |
| 1 | 247933_at | AT5G56980 | expressed protein | 0.43 | 0.75 | 0.22 | 0.20 |
| 1 | 261772_at | AT1G76240 | expressed protein, | 0.40 | 0.57 | 0.07 | 0.16 |
| 1 | 260034_at | AT1G68810 | basic helix-loop-helix (bHLH) family protein | 0.80 | 1.11 | 0.41 | 0.83 |
| 1 | 258091_at | AT3G14560 | expressed protein | 0.59 | 0.81 | 0.35 | 0.50 |
| 1 | 264091_at | AT1G79110 | expressed protein | 0.66 | 1.09 | 0.45 | 0.77 |
| 1 | 254024_at | AT4G25780 | pathogenesis-related protein | 0.12 | 0.74 | 0.18 | 0.26 |
| 1 | 266799_at | AT2G22860 | phytosulfokines 2 (PSK2) | 0.68 | 0.86 | 0.19 | 0.44 |
| 1 | 252387_at | AT3G47800 | aldose 1-epimerase family protein | 0.91 | 1.06 | 0.57 | 0.26 |
| 1 | 258196_at | AT3G13980 | expressed protein | 0.25 | 0.71 | 0.08 | 0.45 |
| 1 | 262531_at | AT1G17230 | leucine-rich repeat family protein | 1.09 | 1.08 | 0.22 | 0.38 |
| 1 | 249467_at | AT5G39610 | no apical meristem (NAM) family protein | 0.72 | 0.65 | 0.35 | 0.22 |
| 1 | 246495_at | AT5G16200 | 50S ribosomal protein-related | 0.37 | 0.70 | 0.10 | 0.20 |
| 1 | 245136_at | AT2G45210 | auxin-responsive protein-related | 0.34 | 0.77 | 0.24 | 0.21 |
| 1 | 258021_at | AT3G19380 | U-box domain-containing protein | 0.67 | 0.70 | 0.48 | 0.27 |
| 1 | 247754_at | AT5G59080 | expressed protein | 0.46 | 0.62 | 0.40 | 0.53 |
| 1 | 245325_at | AT4G14130 | xyloglucan:xyloglucosyl transferase | 0.37 | 0.85 | 0.02 | 0.08 |
| 1 | 261700_at | AT1G32690 | expressed protein | 0.38 | 0.92 | 0.26 | 0.48 |
| 1 | 259751_at | AT1G71030 | Encodes a putative myb family transcription factor | 0.92 | 0.84 | 0.46 | 0.13 |
| 1 | 262259_s_at | AT1G53870; AT1G53890 | [AT1G53870, expressed protein] | 0.43 | 0.89 | 0.51 | 0.77 |
| 1 | 248801_at | AT5G47370 | homeobox-leucine zipper protein 2 (HAT2) | 0.51 | 0.94 | 0.43 | 0.87 |
| 1 | 247074_at | AT5G66590 | allergen V5/Tpx-1-related family protein | 0.53 | 1.21 | 0.31 | 0.58 |
| 1 | 267515_at | AT2G45680 | TCP family transcription factor | 0.50 | 0.91 | 0.46 | 0.82 |
| 1 | 246063_at | AT5G19340 | expressed protein | 0.83 | 0.68 | 0.23 | 0.39 |
| 1 | 266150_s_at | AT2G12290; AT4G19700 | [AT2G12290, expressed protein]; [AT4G19700, expressed protein] | 0.38 | 0.80 | 0.53 | 0.55 |
| 1 | 245276_at | AT4G16780 | homeobox-leucine zipper protein 4 (HAT4)/HD-ZIP protein | 0.54 | 0.62 | 0.42 | 0.51 |
| 1 | 261597_at | AT1G49780 | U-box domain-containing protein | 0.71 | 0.53 | 0.56 | 0.28 |
| 1 | 255538_at | AT4G01680 | myb family transcription factor (MYB55) | 0.21 | 0.51 | 0.14 | 0.14 |
| 1 | 245439_at | AT4G16670 | expressed protein | 0.79 | 0.78 | 0.34 | 0.35 |
| 1 | 251839_at | AT3G54950 | patatin-related, | 0.58 | 0.86 | 0.43 | 0.39 |
| 1 | 258432_at | AT3G16570 | rapid alkalinization factor (RALF) family protein | 0.54 | 0.88 | 0.36 | 0.87 |
| 1 | 251827_at | AT3G55120 | chalcone-flavanone isomerase | 0.94 | 0.98 | 0.39 | 0.68 |
| 1 | 259982_at | AT1G76410 | zinc finger (C3HC4-type RING finger) | 0.54 | 1.61 | 0.16 | 0.43 |
| 1 | 245229_at | AT4G25620 | hydroxyproline-rich glycoprotein family protein | 0.51 | 0.87 | 0.49 | 0.86 |
| 1 | 255177_at | AT4G08040 | 1-aminocyclopropane-1-carboxylate synthase, putative | 0.08 | 0.13 | 0.02 | 0.02 |
| 2 | 258075_at | AT3G25900 | homocysteine S-methyltransferase 1 (HMT-1) | 1.32 | 1.17 | 2.67 | 2.22 |
| 2 | 246584_at | AT5G14730 | expressed protein | 0.38 | 0.80 | 0.53 | 0.55 |
| 2 | 263823_s_at | AT2G40340; AT2G40350 | [AT2G40340, encodes a member of the DREB subfamily A-2 of ERF/AP2 | 1.40 | 1.16 | 3.20 | 1.68 |
| 2 | 245272_at | AT4G17250 | expressed protein | 1.20 | 0.86 | 3.32 | 1.82 |
| 2 | 245119_at | AT2G41640 | expressed protein | 1.96 | 0.84 | 2.53 | 1.43 |

TABLE 1-continued

Fold-change of genes following exposure to BL and ABRASIN (BIK) treatment.

| | | | | 30 min | | 120 min | |
|---|---|---|---|---|---|---|---|
| Cluster | Affymetrix no. | Accession no. | Annotation | BIK | BL | BIK | BL |
| 2 | 266693_at | AT2G19800 | expressed protein | 2.29 | 1.20 | 2.22 | 1.78 |
| 2 | 254204_at | AT4G24160 | hydrolase, alpha/beta fold family protein | 1.42 | 1.13 | 2.29 | 1.14 |
| 2 | 248732_at | AT5G48070 | putative xyloglucan endotransglycosylase/hydrolase | 1.48 | 1.12 | 3.63 | 1.24 |
| 2 | 262072_at | AT1G59590 | expressed protein | 1.99 | 0.95 | 2.08 | 1.03 |
| 2 | 267592_at | AT2G39710 | aspartyl protease family protein | 2.42 | 1.25 | 2.52 | 1.00 |
| 2 | 248164_at | AT5G54490 | calcium-binding EF-hand protein, putative | 0.73 | 0.37 | 3.06 | 1.75 |
| 2 | 251910_at | AT3G53810 | lectin protein kinase | 2.28 | 0.80 | 2.23 | 1.19 |
| 2 | 249188_at | AT5G42830 | transferase family protein | 1.03 | 0.87 | 2.74 | 0.62 |
| 2 | 248134_at | AT5G54860 | integral membrane transporter family protein | 1.69 | 0.92 | 2.01 | 0.82 |
| 2 | 245041_at | AT2G26530 | expressed protein | 1.24 | 0.41 | 1.99 | 0.86 |
| 2 | 261648_at | AT1G27730 | zinc finger (C2H2 type) family protein | 0.56 | 0.18 | 1.06 | 0.71 |
| 2 | 267028_at | AT2G38470 | WRKY family transcription factor | 2.02 | 0.38 | 1.34 | 0.57 |
| 2 | 253044_at | AT4G37290 | expressed protein | 0.95 | 0.90 | 2.45 | 0.40 |
| 2 | 255502_at | AT4G02410 | lectin protein kinase family protein | 2.60 | 0.66 | 1.55 | 0.59 |
| 2 | 249494_at | AT5G39050 | transferase family protein | 1.49 | 1.35 | 1.83 | 0.62 |
| 2 | 245369_at | AT4G15975 | zinc finger (C3HC4-type RING finger) family protein | 2.33 | 1.10 | 3.28 | 1.05 |
| 2 | 249558_at | AT5G38310 | expressed protein | 1.00 | 0.98 | 1.88 | 0.93 |
| 2 | 258282_at | AT3G26910 | hydroxyproline-rich glycoprotein family protein | 2.49 | 1.08 | 1.85 | 0.60 |
| 2 | 252501_at | AT3G46880 | expressed protein | 1.50 | 0.84 | 1.51 | 0.60 |
| 2 | 266265_at | AT2G29340 | short-chain dehydrogenase/reductase (SDR) family protein | 1.55 | 0.85 | 3.73 | 1.29 |
| 2 | 253737_at | AT4G28703 | expressed protein | 1.95 | 0.85 | 6.14 | 0.89 |
| 2 | 255941_at | AT1G20350 | mitochondrial import inner membrane translocase subunit | 1.00 | 0.99 | 2.67 | 1.08 |
| 2 | 256522_at | AT1G66160 | U-box domain-containing protein, | 2.03 | 1.10 | 1.91 | 1.22 |
| 2 | 264746_at | AT1G62300 | WRKY family transcription factor | 1.58 | 0.63 | 0.71 | 0.21 |
| 2 | 260602_at | AT1G55920 | serine O-acetyltransferase | 2.19 | 1.04 | 2.16 | 1.01 |
| 2 | 245662_at | AT1G28190 | expressed protein | 2.79 | 0.66 | 1.65 | 0.58 |
| 2 | 251039_at | AT5G02020 | expressed protein | 1.01 | 0.99 | 2.29 | 0.96 |
| 2 | 256337_at | AT1G72060 | expressed protein | 2.19 | 0.96 | 5.97 | 0.92 |
| 2 | 246858_at | AT5G25930 | leucine-rich repeat family protein | 2.65 | 0.98 | 1.38 | 0.63 |
| 2 | 253414_at | AT4G33050 | calmodulin-binding family protein | 2.38 | 0.99 | 1.58 | 0.57 |
| 2 | 249765_at | AT5G24030 | C4-dicarboxylate transporter/malic acid transport family protein | 2.35 | 1.43 | 1.66 | 1.90 |
| 2 | 247617_at | AT5G60270 | lectin protein kinase family protein | 0.96 | 1.03 | 2.56 | 1.82 |
| 2 | 254294_at | AT4G23070 | rhomboid family protein | 2.00 | 1.02 | 3.80 | 2.03 |
| 2 | 245262_at | AT4G16563 | aspartyl protease family protein | 1.16 | 1.44 | 1.65 | 2.89 |
| 2 | 263652_at | AT1G04330 | expressed protein | 1.17 | 1.04 | 4.41 | 1.30 |
| 2 | 264083_at | AT2G31230 | encodes a member of the ERF (ethylene response factor) | 2.13 | 1.66 | 3.17 | 2.74 |
| 2 | 246401_at | AT1G57560 | myb family transcription factor (MYB50) | 1.19 | 1.04 | 2.65 | 2.45 |
| 2 | 253828_at | AT4G27970 | C4-dicarboxylate transporter/malic acid transport family protein | 2.43 | 1.20 | 3.04 | 1.28 |
| 2 | 262315_at | AT1G70990 | proline-rich family protein | 1.70 | 1.59 | 3.50 | 2.22 |
| 2 | 262124_at | AT1G59660 | nucleoporin family proteinmily | 1.45 | 1.67 | 2.94 | 3.15 |
| 2 | 267393_at | AT2G44500 | expressed protein | 1.26 | 1.16 | 2.19 | 2.06 |
| 2 | 247543_at | AT5G61600 | encodes a member of the ERF (ethylene response factor) | 0.53 | 0.46 | 2.04 | 2.06 |
| 2 | 246200_at | AT4G37240 | expressed protein | 0.79 | 1.23 | 1.45 | 2.33 |
| 2 | 260434_at | AT1G68330 | expressed protein | 1.76 | 0.90 | 2.78 | 1.74 |
| 2 | 247610_at | AT5G60630 | expressed protein | 0.99 | 0.94 | 2.20 | 1.15 |
| 2 | 249752_at | AT5G24660 | expressed protein | 2.43 | 1.33 | 3.61 | 2.26 |
| 2 | 247625_at | AT5G60200 | Dof-type zinc finger domain-containing protein | 1.36 | 0.82 | 3.85 | 1.67 |
| 2 | 254292_at | AT4G23030 | MATE efflux protein-related | 1.60 | 1.37 | 5.25 | 2.20 |
| 2 | 263207_at | AT1G10550 | xyloglucan:xyloglucosyl transferase | 1.26 | 1.34 | 1.66 | 2.19 |
| 2 | 258367_at | AT3G14370 | protein kinase family protein | 1.10 | 2.13 | 2.16 | 3.50 |
| 2 | 263931_at | AT2G36220 | expressed protein | 1.10 | 1.18 | 2.76 | 2.62 |
| 2 | 263150_at | AT1G54050 | 17.4 kDa class III heat shock protein (HSP17.4-CIII | 1.16 | 1.09 | 2.86 | 3.58 |
| 2 | 256453_at | AT1G75270 | dehydroascorbate reductase | 1.16 | 1.27 | 2.62 | 1.66 |
| 2 | 251162_at | AT3G63300 | expressed protein | 1.26 | 1.02 | 2.07 | 1.13 |
| 2 | 267238_at | AT2G44130 | kelch repeat-containing F-box family protein | 1.13 | 1.63 | 7.72 | 6.30 |
| 2 | 251774_at | AT3G55840 | expressed protein | 1.05 | 1.06 | 6.96 | 7.41 |
| 3 | 246781_at | AT5G27350 | sugar-porter family protein 1 (SFP1) | 1.07 | 1.11 | 1.56 | 2.04 |
| 3 | 248419_at | AT5G51550 | phosphate-responsive 1 family protein | 1.02 | 0.86 | 0.41 | 0.37 |
| 3 | 252970_at | AT4G38850 | auxin-responsive protein (SAUR-AC1) | 1.00 | 1.43 | 2.22 | 3.03 |
| 3 | 252972_at | AT4G38840 | auxin-responsive protein (SAUR14) | 1.01 | 1.26 | 1.95 | 2.53 |
| 3 | 265806_at | AT2G18010 | auxin-responsive family protein (SAUR10) | 1.35 | 1.60 | 3.94 | 9.13 |
| 3 | 246926_at | AT5G25240 | expressed protein | 0.74 | 1.21 | 2.16 | 3.69 |
| 3 | 245176_at | AT2G47440 | DNAJ heat shock N-terminal domain-containing protein | 1.07 | 1.31 | 1.64 | 2.23 |
| 3 | 253736_at | AT4G28780 | GDSL-motif lipase/hydrolase family protein | 1.00 | 1.25 | 1.26 | 2.29 |
| 3 | 263325_at | AT2G04240 | zinc finger (C3HC4-type RING finger) family protein | 0.77 | 1.46 | 1.72 | 2.81 |
| 3 | 253103_at | AT4G36110 | auxin-responsive protein | 1.16 | 2.35 | 4.62 | 7.86 |
| 3 | 260287_at | AT1G80440 | kelch repeat-containing F-box family protein | 1.36 | 1.71 | 2.89 | 2.93 |
| 3 | 255931_at | AT1G12710 | F-box family protein | 0.88 | 1.26 | 1.41 | 2.11 |
| 3 | 254424_at | AT4G21510 | F-box family protein | 1.03 | 1.47 | 2.54 | 2.09 |
| 3 | 261265_at | AT1G26800 | zinc finger (C3HC4-type RING finger) family protein, | 1.07 | 1.51 | 4.39 | 6.09 |
| 3 | 267614_at | AT2G26710 | cytochrome p450 family (BAS1) | 0.72 | 1.56 | 2.26 | 5.42 |
| 3 | 252965_at | AT4G38860 | auxin-responsive protein (SAUR16) | 0.79 | 1.38 | 2.27 | 3.40 |
| 3 | 262630_at | AT1G06520 | Encodes a membrane associated mitochondrial localized protein | 1.26 | 1.57 | 2.28 | 3.11 |
| 3 | 265732_at | AT2G01300 | expressed protein | 0.73 | 1.16 | 3.12 | 4.83 |

TABLE 1-continued

Fold-change of genes following exposure to BL and ABRASIN (BIK) treatment.

| Cluster | Affymetrix no. | Accession no. | Annotation | 30 min BIK | 30 min BL | 120 min BIK | 120 min BL |
|---|---|---|---|---|---|---|---|
| 3 | 255037_at | AT4G09460 | myb family transcription factor | 1.50 | 1.30 | 3.27 | 2.76 |
| 3 | 248040_at | AT5G55970 | zinc finger (C3HC4-type RING finger) family protein | 0.96 | 1.03 | 2.56 | 1.82 |
| 3 | 259864_at | AT1G72800 | nuM1-related, contains | 1.15 | 1.08 | 2.15 | 2.85 |
| 3 | 249947_at | AT5G19200 | short-chain dehydrogenase/reductase (SDR) family protein | 1.00 | 1.22 | 1.11 | 2.47 |
| 3 | 252173_at | AT3G50650 | scarecrow-like transcription factor 7 (SCL7) | 1.51 | 1.17 | 2.48 | 1.82 |
| 3 | 266908_at | AT2G34650 | protein kinase PINOID (PID) | 1.04 | 1.54 | 2.52 | 3.26 |
| 3 | 266447_at | AT2G43290 | calmodulin-like protein (MSS3) | 0.81 | 1.24 | 1.45 | 2.99 |
| 3 | 262653_at | AT1G14130 | 2-oxoglutarate-dependent dioxygenase | 1.10 | 1.26 | 2.47 | 1.31 |
| 3 | 261443_at | AT1G28480 | glutaredoxin family protein | 1.02 | 0.99 | 3.97 | 1.38 |
| 3 | 246464_at | AT5G16980 | NADP-dependent oxidoreductase | 1.11 | 1.15 | 3.07 | 1.26 |
| 4 | 247940_at | AT5G57190 | phosphatidylserine decarboxylase | 1.32 | 1.04 | 1.58 | 0.60 |
| 4 | 266835_at | AT2G29990 | pyridine nucleotide-disulphide oxidoreductase family protein | 1.43 | 0.94 | 1.38 | 0.48 |
| 4 | 245051_at | AT2G23320 | WRKY family transcription factor | 1.41 | 0.86 | 1.19 | 0.50 |
| 4 | 248686_at | AT5G48540 | 33 kDa secretory protein-related | 2.45 | 1.01 | 2.03 | 0.55 |
| 4 | 262550_at | AT1G31310 | hydroxyproline-rich glycoprotein family protein | 1.17 | 0.85 | 2.45 | 0.74 |
| 4 | 249480_s_at | AT5G38990; AT5G39000 | [AT5G38990, protein kinase family protein | 1.40 | 0.94 | 2.08 | 0.74 |
| 4 | 252230_at | AT3G49810 | U-box domain-containing protein | 1.29 | 0.89 | 1.12 | 0.56 |
| 4 | 250004_at | AT5G18750 | DNAJ heat shock N-terminal domain-containing protein | 1.91 | 1.03 | 1.26 | 0.56 |
| 4 | 253573_at | AT4G31020 | expressed protein | 2.67 | 1.53 | 5.81 | 0.67 |
| 4 | 246321_at | AT1G16640 | transcriptional factor B3 family protein | 1.14 | 1.02 | 2.20 | 0.95 |
| 4 | 258537_at | AT3G04210 | disease resistance protein (TIR-NBS class), putative, | 2.18 | 0.89 | 3.17 | 1.00 |
| 4 | 258651_at | AT3G09920 | phosphatidylinositol-4-phosphate 5-kinase family protein | 1.56 | 0.94 | 1.07 | 0.42 |
| 4 | 255933_at | AT1G12750 | rhomboid family protein | 1.46 | 1.15 | 1.60 | 0.78 |
| 4 | 257398_at | AT2G01990 | expressed protein, | 1.89 | 0.91 | 2.56 | 1.06 |
| 4 | 249435_at | AT5G39970 | expressed protein | 1.42 | 1.08 | 2.66 | 0.99 |
| 4 | 251832_at | AT3G55150 | exocyst subunit EXO70 family protein | 3.44 | 0.75 | 0.48 | 0.13 |
| 4 | 261382_at | AT1G05470 | endonuclease/exonuclease/phosphatase family protein | 1.42 | 1.04 | 2.59 | 1.05 |
| 4 | 254231_at | AT4G23810 | WRKY family transcription factor | 5.76 | 0.71 | 1.00 | 0.55 |
| 4 | 246993_at | AT5G67450 | zinc finger (C2H2 type) protein 1 (AZF1) | 6.17 | 1.79 | 1.82 | 0.89 |
| 4 | 252047_at | AT3G52490 | heat shock protein-related | 1.17 | 0.93 | 2.41 | 1.08 |
| 4 | 265158_at | AT1G31040 | zinc-binding protein-related | 1.35 | 0.88 | 4.37 | 1.12 |
| 4 | 267171_at | AT2G37590 | Dof-type zinc finger domain-containing protein | 1.52 | 0.90 | 5.81 | 1.19 |
| 4 | 255895_at | AT1G18020; AT1G17990 | [AT1G18020, 12-oxophytodienoate reductase, | 1.31 | 0.80 | 1.78 | 0.50 |
| 4 | 257805_at | AT3G18830 | polyol/cyclitol/monosaccharide-H+-symporte | 1.64 | 1.11 | 2.60 | 1.14 |
| 4 | 253779_at | AT4G28490 | leucine-rich repeat transmembrane protein kinase, putative | 1.20 | 1.00 | 2.30 | 0.78 |
| 4 | 264056_at | AT2G28510 | Dof-type zinc finger domain-containing protein | 1.28 | 0.94 | 1.19 | 0.51 |
| 5 | 252296_at | AT3G48970 | copper-binding family protein | 0.40 | 0.97 | 0.38 | 0.59 |
| 5 | 254809_at | AT4G12410 | auxin-responsive family protein | 0.66 | 1.02 | 0.31 | 0.44 |
| 5 | 258189_at | AT3G17860 | expressed protein | 0.78 | 1.08 | 0.45 | 0.74 |
| 5 | 250598_at | AT5G07690 | myb family transcription factor (MYB29) | 0.58 | 0.82 | 0.27 | 0.40 |
| 5 | 246516_at | AT5G15740 | expressed protein | 0.78 | 0.95 | 0.49 | 0.69 |
| 5 | 248190_at | AT5G54120 | expressed protein | 0.82 | 1.04 | 0.38 | 0.94 |
| 5 | 253629_at | AT4G30450 | glycine-rich protein | 0.84 | 0.88 | 0.39 | 0.59 |
| 5 | 248191_at | AT5G54130 | calcium-binding EF hand family protein | 0.84 | 1.03 | 0.31 | 0.88 |
| 5 | 257746_at | AT3G29200 | chorismate mutase, chloroplast (CM1) | 0.83 | 0.89 | 0.49 | 0.66 |
| 5 | 247774_at | AT5G58660 | oxidoreductase. 2OG-Fe(II) oxygenase family protein | 1.15 | 1.08 | 2.15 | 2.85 |
| 5 | 253483_at | AT4G31910 | transferase family protein | 1.46 | 1.15 | 1.60 | 0.78 |
| 5 | 252646_at | AT3G44610 | protein kinase family protein | 0.83 | 1.05 | 0.38 | 1.03 |
| 5 | 257066_at | AT3G18280 | protease inhibitor/seed storage/lipid transfer protein | 1.03 | 1.06 | 0.39 | 0.92 |
| 5 | 250907_at | AT5G03670 | expressed protein | 0.61 | 0.60 | 0.32 | 0.37 |
| 5 | 253617_at | AT4G30410 | expressed protein | 0.94 | 0.97 | 0.45 | 0.45 |
| 5 | 247177_at | AT5G65300 | expressed protein | 0.31 | 0.25 | 0.25 | 0.36 |
| 5 | 245885_at | AT5G09440 | phosphate-responsive protein, putative | 0.38 | 0.58 | 0.13 | 0.13 |
| 5 | 251072_at | AT5G01740 | expressed protein, | 0.33 | 0.53 | 0.34 | 0.47 |
| 6 | 250012_x_at | AT5G18060 | auxin-responsive protein | 1.00 | 0.76 | 0.46 | 0.28 |
| 6 | 259784_at | AT1G29450 | auxin-responsive protein | 0.99 | 0.75 | 0.61 | 0.37 |
| 6 | 259783_at | AT1G29510 | auxin-responsive protein | 1.02 | 0.77 | 0.50 | 0.36 |
| 6 | 259773_at | AT1G29500 | auxin-responsive protein | 1.01 | 0.79 | 0.61 | 0.39 |
| 6 | 257506_at | AT1G29440 | auxin-responsive family protein | 0.96 | 0.69 | 0.47 | 0.34 |
| 6 | 255403_at | AT4G03400 | auxin-responsive GH3 family protein | 0.81 | 0.59 | 0.77 | 0.48 |
| 6 | 256528_at | AT1G66140 | zinc finger (C2H2 type) family protein | 0.87 | 0.72 | 0.61 | 0.46 |
| 6 | 248282_at | AT5G52900 | expressed protein | 1.70 | 0.74 | 0.96 | 0.50 |
| 6 | 261768_at | AT1G15550 | gibberellin 3-beta-dioxygenase | 1.12 | 0.77 | 1.17 | 0.52 |
| 6 | 259787_at | AT1G29460 | auxin-responsive protein | 1.23 | 0.75 | 0.44 | 0.28 |
| 6 | 265877_at | AT2G42380 | bZIP transcription factor family protein | 1.65 | 0.81 | 0.80 | 0.39 |
| 6 | 245479_at | AT4G16140 | proline-rich family protein | 1.16 | 0.83 | 1.51 | 0.75 |
| 6 | 262040_at | AT1G80080 | leucine-rich repeat family protein | 1.56 | 0.77 | 2.07 | 0.39 |
| 6 | 261203_at | AT1G12845 | expressed protein | 1.66 | 0.98 | 2.71 | 0.47 |
| 6 | 262543_at | AT1G34245 | expressed protein | 1.69 | 1.14 | 5.18 | 0.67 |
| 6 | 253255_at | AT4G34760 | auxin-responsive family protein | 1.80 | 0.81 | 1.61 | 0.62 |
| 7 | 263126_at | AT1G78460 | SOUL heme-binding family protein | 1.01 | 0.88 | 2.50 | 1.49 |
| 7 | 253281_at | AT4G34138 | UDP-glucoronosyl/UDP-glucosyl transferase family protein | 1.52 | 1.17 | 3.16 | 1.74 |
| 7 | 256818_at | AT3G21420 | oxidoreductase, 2OG-Fe(II) oxygenase family protein | 1.13 | 1.11 | 2.39 | 1.29 |
| 7 | 261023_at | AT1G12200 | flavin-containing monooxygenase family protein | 1.44 | 1.11 | 2.20 | 1.40 |

TABLE 1-continued

Fold-change of genes following exposure to BL and ABRASIN (BIK) treatment.

| Cluster | Affymetrix no. | Accession no. | Annotation | 30 min | | 120 min | |
| --- | --- | --- | --- | --- | --- | --- | --- |
| | | | | BIK | BL | BIK | BL |
| 7 | 259875_s_at | AT1G76690; AT1G76680 | [AT1G76690, 12-oxophytodienoate reductase (OPR2) | 1.95 | 0.85 | 6.14 | 0.89 |
| 7 | 247444_at | AT5G62630 | expressed protein | 1.62 | 1.26 | 2.28 | 1.26 |
| 7 | 255443_at | AT4G02700 | sulfate transporter | 1.76 | 1.69 | 2.16 | 1.20 |
| 7 | 264279_s_at | AT1G78820; AT1G78830 | [AT1G78820, curculin-like (mannose-binding) lectin family protein | 1.27 | 0.88 | 1.84 | 0.86 |
| 7 | 245543_at | AT4G15260 | UDP-glucoronosyl/UDP-glucosyl transferase family protein | 1.41 | 1.01 | 1.52 | 0.67 |
| 8 | 255926_at | AT1G22190 | AP2 domain-containing transcription factor | 0.45 | 0.83 | 0.50 | 0.89 |
| 8 | 259364_at | AT1G13260 | DNA-binding protein RAV1 (RAV1) | 0.32 | 0.61 | 0.46 | 0.67 |
| 8 | 259985_at | AT1G76620 | expressed protein | 0.90 | 0.94 | 0.28 | 0.37 |
| 8 | 266124_at | AT2G45080 | cyclin family protein | 0.77 | 0.84 | 0.10 | 0.27 |
| 8 | 250537_at | AT5G08565 | expressed protein | 0.87 | 1.06 | 0.41 | 0.78 |
| 8 | 262050_at | AT1G80130 | expressed protein | 0.90 | 1.04 | 0.18 | 0.36 |
| 8 | 260727_at | AT1G48100 | glycoside hydrolase family 28 protein | 0.92 | 1.06 | 0.38 | 1.16 |
| 8 | 256762_at | AT3G25655 | expressed protein | 1.00 | 0.98 | 0.15 | 0.12 |
| 9 | 247704_at | AT5G59510 | expressed protein | 1.00 | 0.98 | 0.60 | 0.13 |
| 9 | 250493_at | AT5G09800 | U-box domain-containing protein, | 1.04 | 0.80 | 0.80 | 0.30 |
| 9 | 247351_at | AT5G63790 | no apical meristem (NAM) family protein, | 0.88 | 0.49 | 0.69 | 0.27 |
| 9 | 253999_at | AT4G26200 | 1-aminocyclopropane-1-carboxylate synthase | 1.11 | 0.29 | 0.24 | 0.11 |
| 9 | 261892_at | AT1G80840 | WRKY family transcription factor, | 0.43 | 0.27 | 0.20 | 0.05 |
| 9 | 248646_at | AT5G49100 | expressed protein | 0.72 | 0.70 | 0.62 | 0.38 |
| 9 | 251342_at | AT3G60690 | auxin-responsive family protein | 0.91 | 0.87 | 0.29 | 0.27 |
| 10 | 252586_at | AT3G45610 | Dof-type zinc finger domain | 0.94 | 0.90 | 2.56 | 1.05 |
| 10 | 262505_at | AT1G21680 | expressed protein | 0.82 | 1.12 | 2.01 | 1.29 |
| 10 | 260243_at | AT1G63720 | expressed protein | 0.92 | 0.74 | 0.16 | 0.17 |
| 10 | 247601_at | AT5G60850 | Dof-type zinc finger domain-containing protein | 0.51 | 1.09 | 0.64 | 1.10 |
| 10 | 251176_at | AT3G63380 | calcium-transporting ATPase | 0.85 | 0.87 | 0.11 | 0.10 |
| 10 | 246389_at | AT1G77380 | amino acid carrier | 1.32 | 0.94 | 0.99 | 0.40 |
| 10 | 247205_at | AT5G64890 | expressed protein | 1.01 | 0.97 | 2.18 | 0.85 |

REFERENCES

Bao F, Shen J, Brady S R, Munday G K, Asami T and Yang Z (2004). Brassinosteroids interact with auxin to promote lateral root development in *Arabidopsis. Plant Phys.* 134: 1624-1631.

Boudolf V, Barroco R, de Almeida Engler J, Verkest A, Beeckman T, Naudts M, Inze D and De Veylder L (2004) B1-type cyclin-dependent kinases are essential for the formation of stomatal complexes in *Arabidopsis thaliana. Plant Cell* 16, 945-955.

Chinchilla D, Zipfel C, Robatzek S, Kemmerling B, Nürnberger T, Jones J D G, Felix G and Boller T (2007). A flagellin-induced complex of the receptor FLS2 and BAK1 initiates plant defence. *Nature* 448 (7152): 497-500

Choe, S. et al. (1998) The DWF4 gene of Arabisopsis encodes a cytochrome P450 that mediates multiple 22α-hydroxylation steps in brassinosteroid biosynthesis. *Plant Cell* 10, 231-243.

Clouse, S. D., Langford, M. and McMorris, T. C. A. (1996) A brassinosteroid-insensitive mutant in *Arabidopsis thaliana* exhibits multiple defects in growth and development. *Plant Physiol.* 111, 671-678

Clouse, S. D. (2002) Brassinosteroid signal transduction: clarifying the pathway from ligand perception to gene expression. *Mol Cell* 10, 979-982.

De Veylder L, Beeckman T, Beemster G T, Krols L, Terras F, Landrieu I, van der Schueren E, Maes S, Naudts M, Inze D (2001) Functional analysis of cyclin-dependent kinase inhibitors of *Arabidopsis. Plant Cell* 13: 1653-1668

Eulgem T and Somssich I E (2007). Networks of WRKY transcription factors in defense signaling. *Curr Op in Plant Biol,* 10:366-371.

Fankhauser, C, Yeh, K. C., Lagarias, J. C., Zhang, H., Elich, T. D. and Chory, J. (1999) PKS1, a substrate phosphorylated by phytochrome that modulates light signaling in *Arabidospsis. Science* 284, 1539-1541.

Friedrichsen D M, Joazeiro C A P, Li J, Hunter T, and Chory J (2000) Brassinosteroid-insensitive-1 is ubiquitously expressed leucine-rich receptor serine/threonine kinase. *Plant Physiol.* 123, 1247-1255.

Goda H, Shimada Y, Asami T, Fujioka S and Yoshida S (2002). Microarray analysis of brassinosteroid-regulated genes in *Arabidopsis. Plant Physiol.* 130: 1319-1334.

Goda H, Sawa S, Asami T, Fujika s, Shimada Y and Yoshida S (2004). Comprehensive comparison of auxin-regulated and brassinosteroid-regulated genes in *Arabidopsis. Plant Physiol.* 134: 1555-1573.

Hara K, Kajita R, Torii K U, Bergmann D C and Kakimoto T (2007). The secretory peptide gene EPF1 enforces the stomatal one-cell-spacing rule. *Genes Dev* 21:1720-1725.

He, J. X., Gendron, J. M., Sun, Y., Gampala, S. S. L., Gendron, N., Sun, C. Q. and Wang, Z. Y. (2005) BZR1 is a transcriptional repressor with dual roles in brassinosteroid homeostasis and growth responses. *Science,* 307, 1634-1638.

Jefferson R A, Kavanagh T A, Bevan M W (1987) GUS fusions: β-glucuronidase as a sensitive and versatile gene fusion marker in higher plants. *EMBO J* 6: 3901-3907.

Jinn T-L, Stone J M and Walker J C (2000). HAESA, an *Arabidopsis* leucine-rich repeat receptor kinase, controls floral organ abscission. *Genes Dev* 14: 108-117.

Jonak, C. and Hirt, H. (2002) Glycogen synthase kinase 3/SHAGGY-like kinases in plants: an emerging family with novel functions. *Trens Plant Sci,* 7, 457-461.

Kemmerling B, Schwedt A, Rodriguez P, Mazzotta S, Frank M, Qamar S, Mengiste T, Betsuyaku S, Parker J, Müssig C. Thomma B P, Albrecht C, de Vries S C, Hirt H, Nürnberger T. (2007). The BRI1-associated kinase 1, BAK1, has a brassinolide-independent role in plant cell-death control. *Current Biology* 17: 1116-1122

Khripach, V., Zhabinskii, V and De Groot, A. (2000) *Annal of Botany* 86, 441-447.

Li, J., Nam, K. H., Vafeados, D. & Chory, J. (2001). BIN2, a new brassinosteroid-insensitive locus in *Arabidopsis*. *Plant Physiol* 127, 14-22.

Li J, Brader G. and Palva E T (2004). The WRKY70 Transcription Factor: A Node of Convergence for Jasmonate-Mediated and Salicylate-Mediated Signals in Plant Defense. *Plant Cell*, 16(2): 319-331.

Li, J. and Deng, X. W. (2005) It runs in the family: regulation of brassinosteroid signalling by BZR1-BAS1 class of transcription factors. *Trens Plant Sci* 10, 266-268.

Li, J. and Nam, K. H. (2002) Regulation of brassinosteroid signalling by a GSK3/SHAGGY-like kinase. *Science* 295, 1299-1301.

Maere S, Heymans K and Kuiper M (2005). BINGO: a cytoscape plug-in to assess overrepresentation of gene ontology categories in biological networks. *Bioinformatics* 21: 3448-3449.

Mathur J, Molnar G, Fujioka S, Takatsuto S, Sakurai A, Yokota T, Adam G, Voigt B, Nagy F, Maas C, Schell J, Koncz C and Szekeres M (1998). Transcription of the *Arabidopsis* CPD gene, encoding a steroidogenic cytochrome P450, is negatively controlled by brassinosteroids. *Plant J.* 14:593-602.

Mattsson J, Ckurshumova W and Berleth T (2003). Auxin signaling in *Arabidopsis* leaf vascular development. *Plant Phys.* 131:1327-1339.

Mora-Garcia, S., Vert, G., Yin, Y., Cano-Delgado, A., Cheong, H. & Chory, J. (2004)

Nuclear protein phosphatases with Kelch-repeat domains modulate the response to brassinosteroids in *Arabidopsis*. *Genes Dev* 18, 448-460.

Mussig C, Fischer S and Altmann T (2002). Brassinosteroid-regulated gene expression. *Plant Phys.* 129:1241-1251.

Nadeau J A and Sack F D (2002) Control of stomatal distribution on the *Arabidopsis* leaf surface. *Science* 296, 1697-1700.

Nemhauser J L, Mocker T C and Chory J (2004). Interdependency of brassinosteroid and auxin signaling in *Arabidopsis*. *PLOS Biol.* 2(9): e258.

Nemhauser J L, Hong F and Chory J (2006). Different plant hormones regulate similar processes through largely non-overlapping transcriptional responses. *Cell* 126: 467-475.

NET, M. M. et al. (1999) BAS1: a gene regulationg brassinosteroid levels and Light responsiveness in *Arabidopsis*. *Proc. Natl. Acad. Sci USA* 96, 15316-15326.

Tanaka, K. et al. (2005) Brassinosteroid homeostasis in *Arabidopsis* is ensured by feedback expressions of multiple genes envolved in its metabolism. *Plant Physiol* 138, 1117-1125.

Scarpella E, Marcos D, Friml J and Berleth T (2006). Control of leaf vascular patterning by polar auxin transport. *Genes Dev.* 20:1015-1027.

Shimada, Y et al. (2003) Organ specific expression of brassinosteroid-biosynthetic genes and distribution of endogeneous brassinosteroids in *Arabidopsis*. Plant Physiol 131, 287-297.

Szekeres M, Nemeth K, Koncz-Kalman Z, Mathur J, Kauschmann A, Altmann T, Redei G P, Nagy F, Schell J and Koncz C (1996) Brassinosteroids rescue the deficiency of CYP90, a cytochrome P450, controlling cell elongation and de-etiolation in *Arabidopsis*. *Cell* 85, 171-182.

Vert, G., Nemhauser, J. L., Geldner, N., Hong, F. and Chory, J. (2005). Molecular mechanisms of steroid hormona signaling in plants. *Annu Rev CII Dev Biol* 21, 177-201.

Vert, G. & Chory, J. (2006) Downstream nuclear events in brassinosteroid signalling. *Nature* 441, 96-100.

Wang, X. & Chory, J. (2006). Brassinosteroids regulate dissociation of BKI1, a negative regulator of BRI1 signaling, from the plasma membrane. *Science* 313, 1118-1122 (2006).

Wang, Z. Y., Wang, Q., Chong K., Wang, F, Wang, L. Bai, M and Jia, C. (2006). The brassinosteroid signal transduction pathway. *Cell Research*, 16, 427-434.

Yanagisawa S (2002). The Dof family of plant transcription factors. *Trends in Plant Science* 7 (12): 555-560.

Yoo, M. J. et al. (2006) Phylogenetic diversification of glycogen synthase kinase 3/SHAGGY-like kinase genes in plants. *BMC Plant Biol* 6, 3.

The invention claimed is:

1. A method of inducing gene expression, the method comprising:
applying to a plant a non-steroidal, monocyclic brassinosteroid mimetic, having the formula

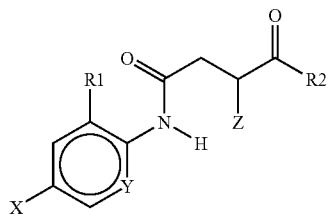

wherein (a) X represents hydrogen or a halogen (b) Y represent carbon or nitrogen (c) Z represents hydrogen or a positively charged nitrogen (d) $R_1$ represents hydrogen or a methyl group and (e) $R_2$ represents hydrogen, a hydroxyl, methyl or carboxy group.

2. A method of inducing brassinosteroid depending, BRI1 independent, gene expression, the method comprising applying to a plant a non-steroidal, monocyclic compound selected from a group consisting of
4-[(5-fluoro-2-pyridinyl)amino]-4-oxobutanoic acid,
4-[(5-chloro-2-pyridinyl)amino]-4-oxobutanoic acid,
4-[(5-bromo-2-pyridinyl)amino]-4-oxobutanoic acid, and
4-[(5-iodo-2-pyridinyl)amino]-4-oxobutanoic acid,
to induce said gene expression.

3. The method according to claim 1, wherein the non-steroidal, monocyclic compound is selected from a group consisting of 4-[(5-fluoro-2-pyridinyl)amino]-4-oxobutanoic acid, 4-[(5-chloro-2-pyridinyl)amino]-4-oxobutanoic acid, 4-[(5-bromo-2-pyridinyl)amino]-4-oxobutanoic acid, and 4-[(5-iodo-2-pyridinyl)amino]-4-oxobutanoic acid.

* * * * *